(12) United States Patent
Schiestl et al.

(10) Patent No.: US 9,045,474 B2
(45) Date of Patent: Jun. 2, 2015

(54) COMPOUNDS AND COMPOSITIONS FOR MITIGATING TISSUE DAMAGE AND LETHALITY

(75) Inventors: Robert H. Schiestl, Encino, CA (US); Yelena O. Rivina, Los Angeles, CA (US); Michael E. Jung, Los Angeles, CA (US); Robert Damoiseaux, Beverly Hills, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 13/813,923

(22) PCT Filed: Aug. 3, 2011

(86) PCT No.: PCT/US2011/046451
§ 371 (c)(1),
(2), (4) Date: May 20, 2013

(87) PCT Pub. No.: WO2012/018932
PCT Pub. Date: Feb. 9, 2012

(65) Prior Publication Data
US 2013/0231518 A1    Sep. 5, 2013

Related U.S. Application Data

(60) Provisional application No. 61/370,386, filed on Aug. 3, 2010.

(51) Int. Cl.
*C07D 405/14* (2006.01)
*A61K 31/4704* (2006.01)
*A61K 31/4709* (2006.01)
(Continued)

(52) U.S. Cl.
CPC .............. *C07D 471/04* (2013.01); *A61K 31/00* (2013.01); *A61K 31/381* (2013.01); *A61K 31/437* (2013.01); *A61K 31/4709* (2013.01); *G01N 33/5088* (2013.01); *G01N 2800/40* (2013.01); *A61K 45/06* (2013.01); *A61N 5/10* (2013.01);
(Continued)

(58) Field of Classification Search
CPC ............................ C07D 471/04; A61K 31/437
USPC ......................................... 514/300; 546/121
See application file for complete search history.

(56) References Cited

U.S. PATENT DOCUMENTS

2004/0023972 A1    2/2004  Sundermann et al.
2004/0265231 A1    12/2004 Blumenthal et al.
2009/0163545 A1*   6/2009  Goldfarb ........................ 514/312

FOREIGN PATENT DOCUMENTS

DE   10 2007 040336 A1   3/2009
WO   WO 01-98290 A2      12/2001
(Continued)

OTHER PUBLICATIONS

Wolff, Manfred E. "Burger's Medicinal Chemistry, 5ed, Part I", John Wiley & Sons, 1995, pp. 975-977.*
(Continued)

*Primary Examiner* — John Mabry
*Assistant Examiner* — Daniel Carcanague
(74) *Attorney, Agent, or Firm* — David P. Halstead; Foley Hoag LLP

(57) ABSTRACT

Embodiments of the present invention provide compounds and compositions thereof, which are effective for mitigating tissue damage or lethality induced by an agent, and methods of making and using the same.

12 Claims, 13 Drawing Sheets

(51) Int. Cl.

| | |
|---|---|
| A61P 39/02 | (2006.01) |
| C07D 471/04 | (2006.01) |
| A61K 31/00 | (2006.01) |
| A61K 31/381 | (2006.01) |
| A61K 31/437 | (2006.01) |
| G01N 33/50 | (2006.01) |
| A61K 45/06 | (2006.01) |
| A61N 5/10 | (2006.01) |
| C07D 333/38 | (2006.01) |
| C07D 409/12 | (2006.01) |
| C12Q 1/02 | (2006.01) |

(52) U.S. Cl.
CPC ............ *C07D 333/38* (2013.01); *C07D 409/12* (2013.01); *C12Q 1/025* (2013.01)

(56) References Cited

FOREIGN PATENT DOCUMENTS

| | | |
|---|---|---|
| WO | WO 2006-101455 A1 | 9/2006 |
| WO | WO 2007-067711 A2 | 6/2007 |
| WO | WO-2007/076055 A2 | 7/2007 |
| WO | WO 2008-016648 A2 | 2/2008 |
| WO | WO 2009061856 * | 5/2009 |
| WO | WO 2010-032195 A1 | 3/2010 |
| WO | WO-2010/116302 A1 | 10/2010 |
| WO | WO 2012-018932 A2 | 2/2012 |

OTHER PUBLICATIONS

Banker, G.S. et al, "Modern Pharmaceutics, 3ed.", Marcel Dekker, New York, 1996, pp. 451 and 596.*
Dumont, Expert Opinion Ther. Patents, 2010, 20, 73-101.*
Goldfarb; US 20090163545, Chemical Abstracts record for registry No. 581069-79-6, dated Jun. 25, 2009.*
Chemical Abstracts STN Record for RN 943071-37-2, entered Jul. 22, 2007.*
Blackburn, Christopher, et al; "A novel dealkylation affording 3-aminoimidazo[1.2-a]pyridines: access to new substitution patterns by solidphase synthesis"; Tetrahedron letters; (2000); vol. 41, No. 10; pp. 1495-1500.
U.S. Appl. No. 61/370,386, filed Aug. 3, 2010, Robert H. Schiestl, et al.
Dimauro, Erin F., et al.; "Rapid Synthesis of 3-Aminoimidazopyridines by a Microwave-Assisted Four-Component Coupling in One Pot"; Journal of Organic Chemistry; (2007); vol. 72, No. 3; pp. 1013-1016.
Ireland, Sarah M., et al.; "Microwave-assisted multi-component synthesis of fused 3-aminoimidazoles"; Tetrahedron letters; (2003) vol. 44, No. 23; pp. 4369-4371.
Kercher, Timothy, et al.; "Diversification of the Three-Component Coupling of 2-Aminoheterocycles, Aldehydes, and Isonitriles: Efficient Parallel Synthesis of a Diverse and Druglike Library of Imidazo- and Tetrahydroimidazo[1,2-a] Heterocycles"; Journal of Combinatorial Chemistry; (2007); vol. 9, No. 6; pp. 1177-1187.
Rousseau, Amanda L., et al.; "Multicomponent synthesis of imidazo[1,2-a] pyridines using catalytic zinc chloride"; Tetrahedron letters; (2007); vol. 48, No. 23; pp. 4079-4082.
International Search Report and Written Opinion uner Patent Cooperation Treaty (PCT) for PCT/US2011/046451; Dated Mar. 9, 2012; 14 pages.
Hafer, K. et al., "Cell Cycle Dependence of Ionizing Radiation-Induced DNA Deletions and Antioxidant Radioprotection in *Saccharomyces cerevisiae*", Radiation Research, 173(6):802-808 (Radiation Research Society, USA, 2010).
Hershman, J. M. et al., "Prevention of DNA Double-Strand Breaks Induced by Radioiodide-131I in FRTL-5 Thyroid Cells", *Endocrinology*, 152(3):1130-1135 (The Endocrine Society, USA, Dec. 29, 2010).
Kim, K. et al., "High throughput screening of small molecule libraries for modifiers of radiation responses", *Int. J. Radiat. Biol.*, 87(8):839-845 (Los Angeles, CA, USA, Aug. 2011).
Extended European Search Report from corresponding application EP 11815272.7 dated Jul. 1, 2013.

* cited by examiner

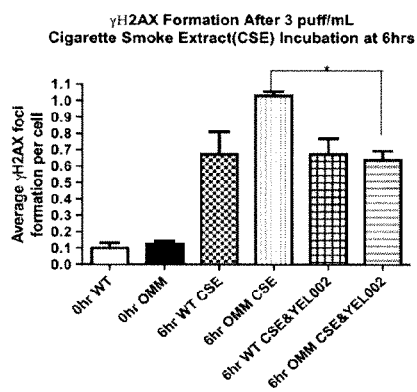
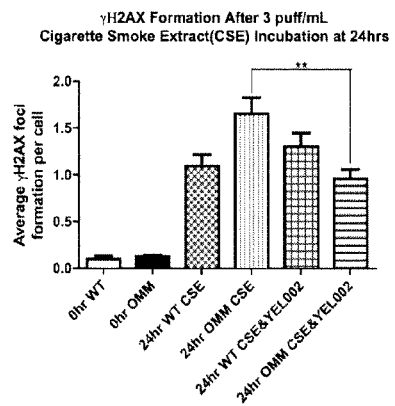
Figures 29a  Figure 29b
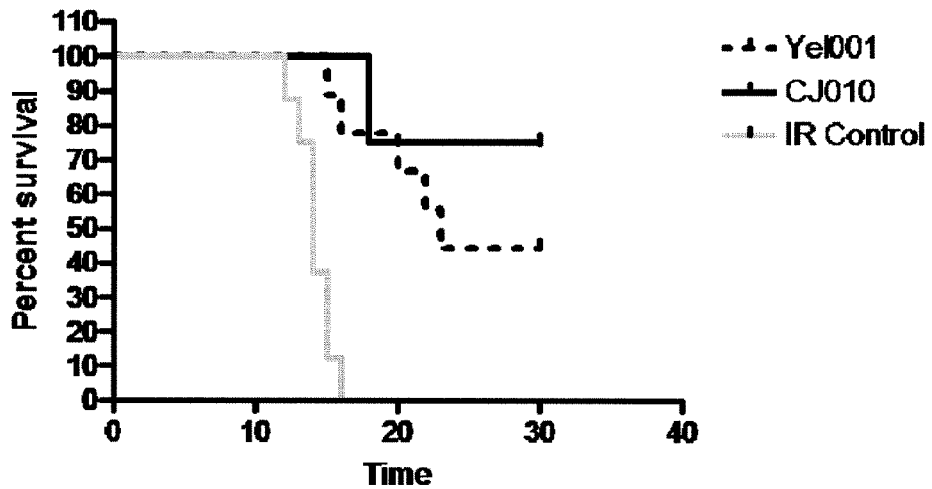
Figure 30
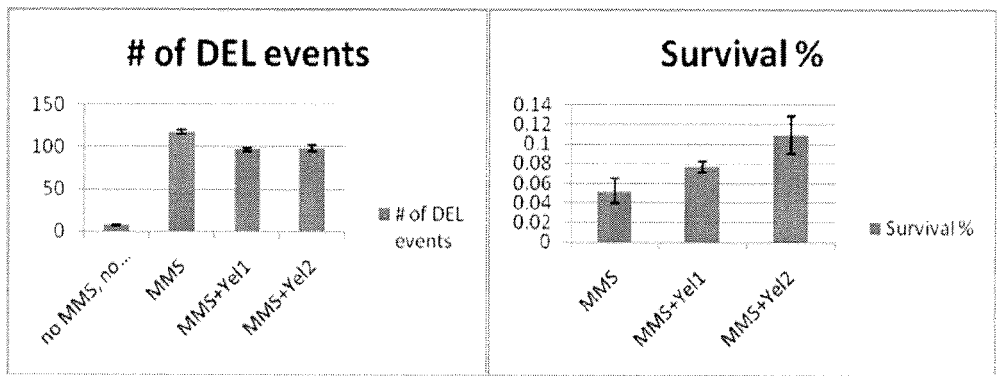
Figure 31

COMPOUNDS AND COMPOSITIONS FOR MITIGATING TISSUE DAMAGE AND LETHALITY

CROSS-REFERENCE TO RELATED APPLICATIONS

This application is a U.S. National Phase of PCT/US2011/046451, entitled "COMPOUNDS AND COMPOSITIONS FOR MITIGATING TISSUE DAMAGE AND LETHALITY" and filed on Aug. 3, 2011, which claims the benefit of U.S. Provisional Patent Application Ser. No. 61/370,386, entitled "COMPOUNDS FOR MITIGATING RADIATION-INDUCED TISSUE DAMAGE AND LETHALITY" and filed on Aug. 3, 2010, the disclosures of which are incorporated herein by reference on their entirety by reference for all purposes.

STATEMENT AS TO RIGHTS TO INVENTIONS MADE UNDER FEDERALLY SPONSORED RESEARCH AND DEVELOPMENT

This invention was made with Government support under Grant No. A1067769, awarded by the National Institutes of Health. The Government has certain rights in this invention.

FIELD OF THE INVENTION

The present invention generally relates to compounds for radiation-induced tissue damage and lethality, compositions comprising these compounds and methods of making and using the same.

BACKGROUND OF THE INVENTION

The recent tragic nuclear power plant accidents in Japan caused severe leaks of radioactive Iodine-131 and Cesium-137 and widespread exposure scare of radiation. In addition, the global use and storage of radioactivity is increasing rapidly. Millions of radioactive sealed sources are used around the world for legitimate and beneficial commercial applications such as cancer treatment, food and blood sterilization, oil exploration, remote electricity generation, radiography, and scientific research. These applications use isotopes such as Cesium-137, Cobalt-60, Strontium-90, Americium-241, Iridium-192, Plutonium-238, Plutonium-239, Curium-244, Radium-226, and Californium-252. Many of these radiological sources at sites around the world are no longer needed and have been abandoned or orphaned; others are poorly guarded, making the risk of theft or sabotage significant. Currently, there are tens of thousands of civilian locations worldwide with radioactive material, about 5,000 of which contain sources of 1,000 curies or greater (Office of Global Threat Reduction (NA-21). GTRI Strategic Plan, release date January 2007. 955 L'Enfant Plaza, Washington, D.C. 20585. Biopulos, Ioanna et al. The Office of Global Threat Reduction: reducing the global threat from radiological dispersal devices. 2007. JNMM Volume 35 Issue 3 PP 36-40). Beyond the public safety concerns are the clinical implications of radiation use.

Outside the radiation therapy clinic there is also significant relevance to identifying and characterizing novel compounds that protect cells from radiation induced cell death. Fundamental to radiation exposure and injury is DNA strand breaks, resulting in genetic instability and DNA deletions which are involved in cell death, cellular dysfunction, as well as long-term consequences such as birth defects and cancer.

There are currently only 5 agents approved by the FDA for radiation protection, and none are approved for non clinical use. However, out of these, only one agent is classified as a cytoprotectant (Amifostine™), and this agent, along with current leads, have demonstrated poor toxicity profiles (see, e.g., Seed, T. M., Health Phys, 2005. 89(5): p. 531-45; Brizel, D. M J Clin Oncol, 2007. 25(26): p. 4084-9), which is a common shortcoming with all current small molecule leads in this area. The other agents are Potassium Iodide, Zn-DTPA (Trisodium zinc diethylenetriaminepentaacetate) and Prussian Blue Ferric III/hexacyanoferrate II as chelators used for isotope exposure, and Granisetron™ as an anti-emetic.

Thus, there is a need for novel drugs used for the prophylaxis, mitigation and treatment of radiation injury.

The embodiments described below address the above mentioned problems and needs.

SUMMARY OF THE INVENTION

In one aspect of the present invention, it is provided a compound, which is effective for mitigating tissue damage and lethality induced by an agent. The compound can be a synthetic compound or a natural product in a substantially purified form. The compound also includes a pharmaceutically acceptable salt thereof, a prodrug thereof, a hydrate thereof, a solvate thereof, or a polymorphic crystal thereof.

In some embodiments of the compound, the compound comprises a structure of Formula I or Formula II:

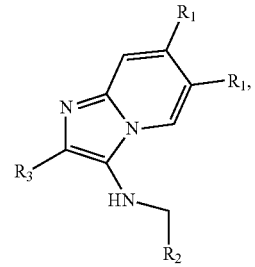

(Formula I)

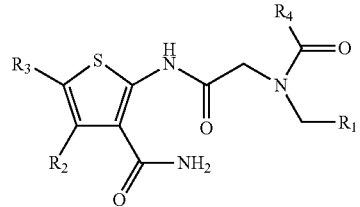

(Formula II)

where:

in Formula I, each $R_1$, $R_2$ and $R_3$ are independently hydrogen, straight chain or branched C1-C20 alkyl, alkenyl, or alkynyl, which is substituted or unsubstituted, cyclo alkyl, cyclo alkenyl, heterocyclic alkyl, or heterocyclic alkenyl, which is substituted or unsubstituted, phenyl, substituted phenyl, aryl, substituted aryl, amino, amido, F, Cl, Br, I, nitro, hydroxyl, thiol, alkylthio, selenol, alkylselenyl, silyl, siloxy, boryl, carboxylic acid, sulfonyl, —$SO_4H$, —$BH_2$, alkoxy, or acyl groups along with a list of the following exemplary substitutions:

Each $R_1$ independently=one or more of the following $NH_2$, OH, OMe, Me, H, $CH_2OH$, $BH_2$, SMe,

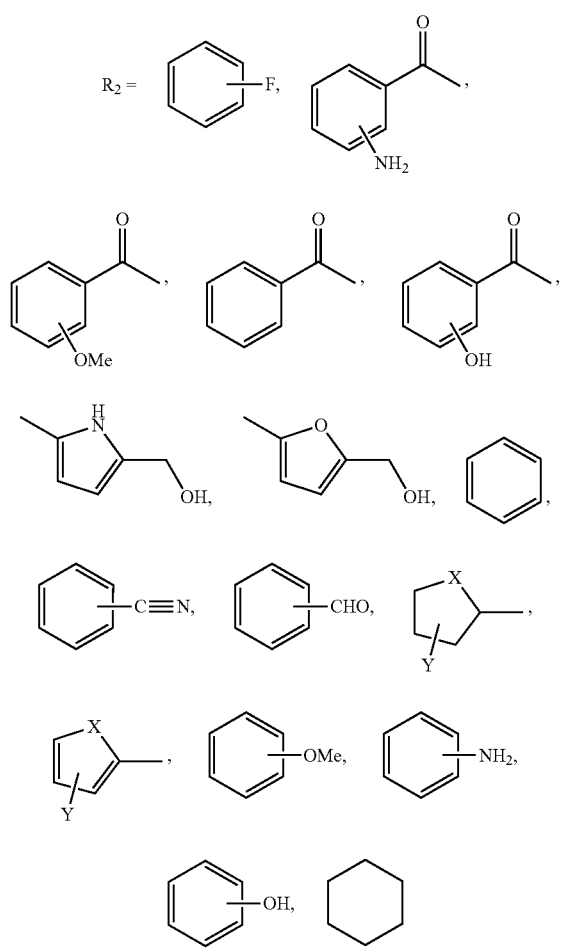

X=S, HN, O, BH, CH₂;
Y=NH₂, OH, OMe, Me, H, CH₂OH, BH₂, SeMe, SMe

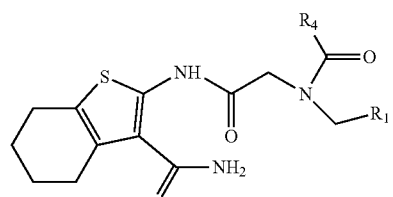

X=S, HN, O, BH, CH₂.
Y=NH₂, OH, OMe, Me, H, CH₂OH, BH₂, SeMe, SMe
and in Formula II, $R_1$, $R_2$, $R_3$, and $R_4$ are independently hydrogen, straight chain or branched C1-C20 alkyl, alkenyl, or alkynyl, which is substituted or unsubstituted, cyclo alkyl, cyclo alkenyl, heterocyclic alkyl, or heterocyclic alkenyl, which is substituted or unsubstituted, phenyl, substituted phenyl, aryl, substituted aryl, amino, amido, F, Cl, Br, I, nitro, hydroxyl, thiol, alkylthio, selenol, alkylselenyl, silyl, siloxy, boryl, carboxylic acid, sulfonyl, —SO₄H, alkoxy, or acyl groups along with a list of the following exemplary substitutions:

$R_1$=$R_4$ and are:

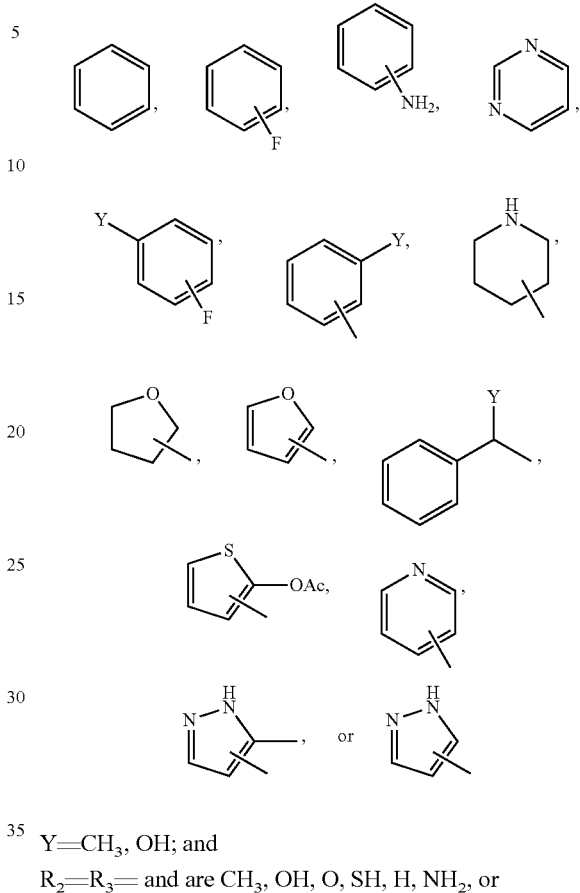

Y=CH₃, OH; and
$R_2$=$R_3$= and are CH₃, OH, O, SH, H, NH₂, or

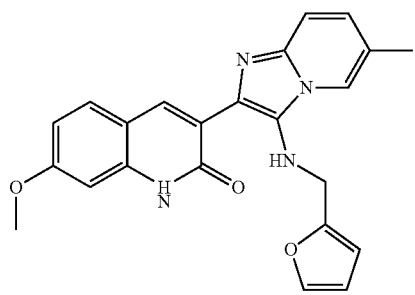

In some embodiments of the compound, the compound has a Tanimoto coefficient at least 0.7 or higher based on a compound of Formula IA, Formula IIA or Formula IIB:

(Formula IA)

(Formula IIA)

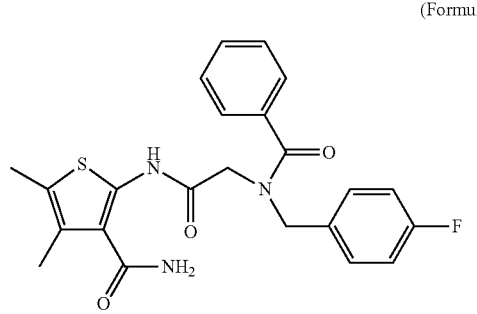

(Formula IIB)

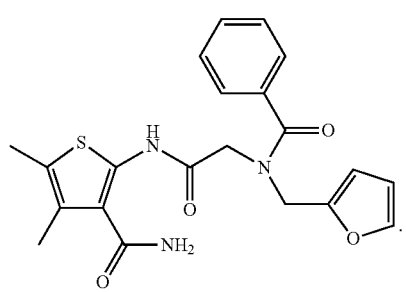

The tissue damage or lethality can be induced by radiation of any kind. In some embodiments, the radiation is radiation by a radioactive element (also referred to as particle radiation such as radiation by radioactive iron atoms, cobalt atoms, etc), alpha radiation, beta radiation, gamma radiation, neutron radiation, x radiation, or ultraviolet radiation.

In some embodiments of the compound, the tissue damage or lethality is induced by radiation therapy.

In some embodiments of the compound, the tissue damage or lethality is of a condition selected from conditions related to radiation-induced lethality, conditions related to radiation-induced genotoxic and cytotoxicity, conditions related to radiation-induced damage to healthy tissues during radiation therapy, conditions related to radiation-induced persistent genetic instability, conditions related to ultraviolet (UV) radiation-induced damage, conditions related to damage to tissue induced by chemical carcinogens, radiation-induced cancer, spontaneous cancer, or aging.

In some embodiments of the compound, the compound is selected from

Formula IA

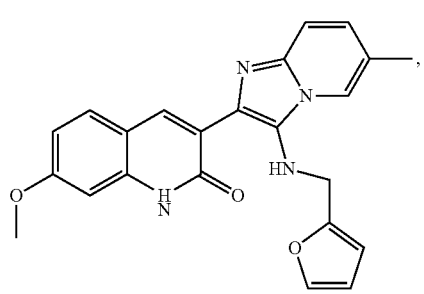

Formula IB

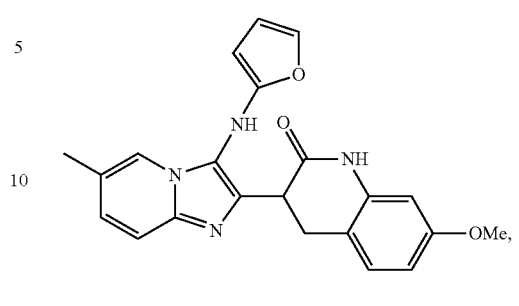

Formula IC

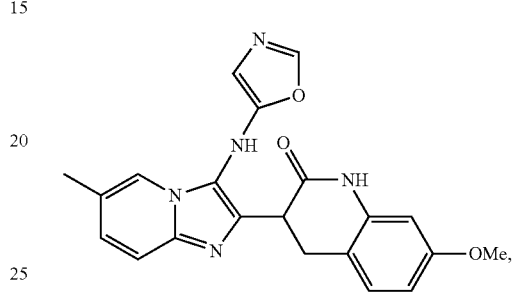

Formula ID

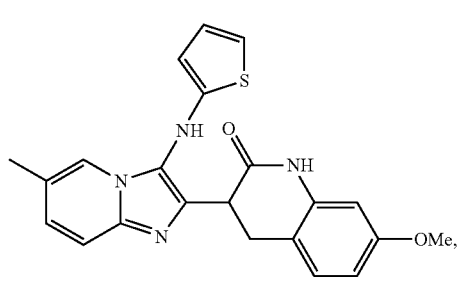

Formula IE

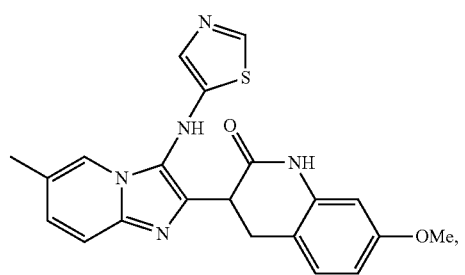

Formula IF

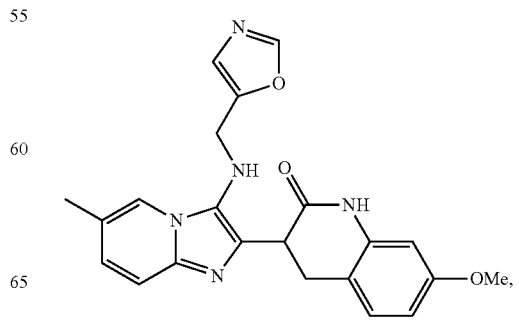

Formula IG

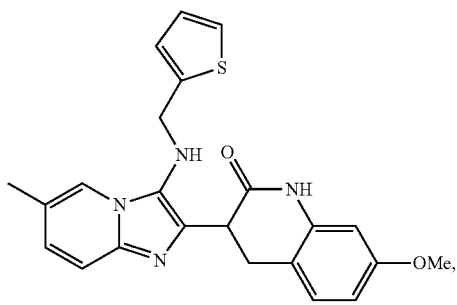

Formula IH

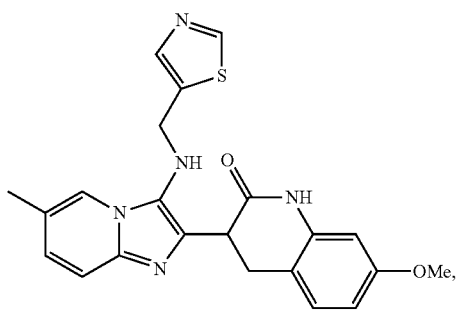

Formula IIA

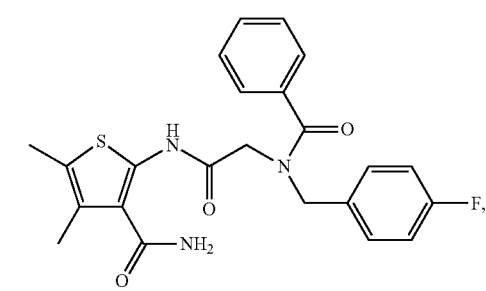

Formula IIB

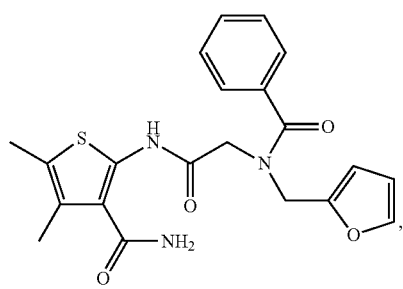

or a combination of the compounds of Formula IA-IH, Formula IIA, or Formula IIB.

In some embodiments of the compound, the compound of the various embodiments above includes a pharmaceutically acceptable salt thereof, or a prodrug thereof.

In another aspect of the present invention, it is provided a composition, which composition comprising a compound of the various embodiments disclosed herein. The composition comprises the compound in an amount effective for mitigating tissue damage or lethality induced by an agent. In some embodiments, the composition includes a compound in an effective amount for a condition selected from conditions related to radiation-induced lethality, conditions related to radiation-induced genotoxicity and cytotoxicity, conditions related to radiation-induced damage to healthy tissues during radiation therapy, conditions related to radiation-induced persistent genetic instability, conditions related to ultraviolet (UV) radiation-induced damage, conditions related to damage induced by chemical carcinogens, radiation-induced cancer, spontaneous cancer, or aging.

In some embodiments of the composition, the composition can further optionally include at least one other therapeutic agent.

In some embodiments of the composition, the composition of various embodiments disclosed herein further comprises an excipient.

In some embodiments of the composition, the composition of various embodiments disclosed herein further comprises a pharmaceutically acceptable carrier.

The composition of various embodiments disclosed herein can be formulated into a formulation for local delivery or systemic delivery. In some embodiments, the composition is formulated into a formulation for oral administration, injection, topical administration, implant, or pulmonary administration.

The composition of various embodiments disclosed herein can be a therapeutic composition, a cosmetic composition, or a dietary supplement.

In a further aspect of the present invention, it is provided a method of screening for a compound effective as a radiation protective/mitigating agent. The method comprises:
generating a screening system capable of screening a compound against radiation-induced cell killing, genetic instability, or both; and
subject a compound to the screening, and
identifying a compound as radiation protective if the compound significantly reduces radiation induced cell killing or genetic instability as compared to a control.

In some embodiments of the method, the compound has a structure of Formula I or Formula II.

In a further aspect of the present invention, it is provided a method of preparing a compound. The method comprises preparing a compound according to the various embodiments disclosed above.

In a further aspect of the present invention, it is provided a method of preparing a composition. The method comprises providing a compound which is effective for mitigating tissue damage and lethality induced by an agent, and forming the composition of the various embodiments disclosed herein. The compound is as in the various embodiments disclosed herein.

In a further aspect of the present invention, it is provided a method of treating, preventing, or ameliorating a condition. The method comprises administering to a subject a compound or a composition according to the various embodiments of disclosed herein.

In some embodiments, the condition is selected from conditions related to radiation-induced lethality, conditions related to radiation-induced genotoxicity and cytotoxicity, conditions related to radiation-induced damage to healthy tissues during radiation therapy, conditions related to radiation-induced persistent genetic instability, conditions related to ultraviolet (UV) radiation-induced damage, conditions related to damage induced by chemical carcinogens, radiation-induced cancer, spontaneous cancer, or aging.

In a still further aspect of the present invention, it is provided a method of radiation therapy. The method comprises:
administering to a subject a compound of invention, and
administering to the subject a radiation;
wherein the subject has a medical condition capable of being treated or ameliorated by radiation.

In some embodiments, the compound is included in a composition.

In some embodiments, the composition further includes an optional second agent.

In some embodiments of the method, the medical condition is cancer, e.g., skin cancer or leukemia.

BRIEF DESCRIPTION OF THE DRAWINGS

FIG. 29a (left) shows a significant decrease in the amount of average γH2AX per cell in OMM lymphocytes at p<0.05. FIG. 29b (right) shows that YEL 002 incubation significantly decreases the amount of average γH2AX per cell in OMM lymphocytes p<0.01.

FIG. 30 shows the results of tests where C3H (n=8 in each group) were irradiated and treated at the 5×24 treatment protocol with Yel001 and CJ-10 s.c.

FIG. 31 shows addition of MMS to DEL RS112 tester strain induces cell death and genotoxicity that can be mitigated with Yel001 and Yel002 administration 1 hrs after exposure to MMS.

DETAILED DESCRIPTION OF THE INVENTION

Figure 1:
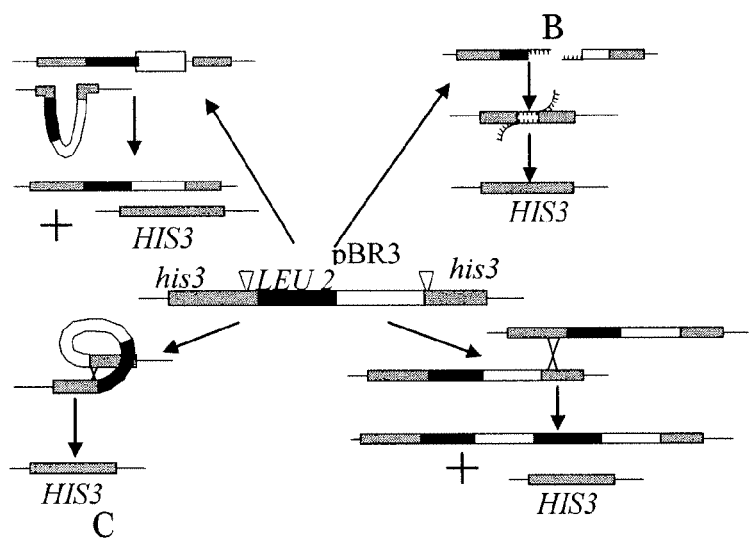
FIG. 1 is an outline of the structure and possible mechanisms for reversion of the yeast intrachromosomal recombination (DEL) system. A: Sister chromatid conversion; B: single strand annealing; C: intrachromosomal crossing over; D: unequal sister chromatid exchange.
Figure 2:
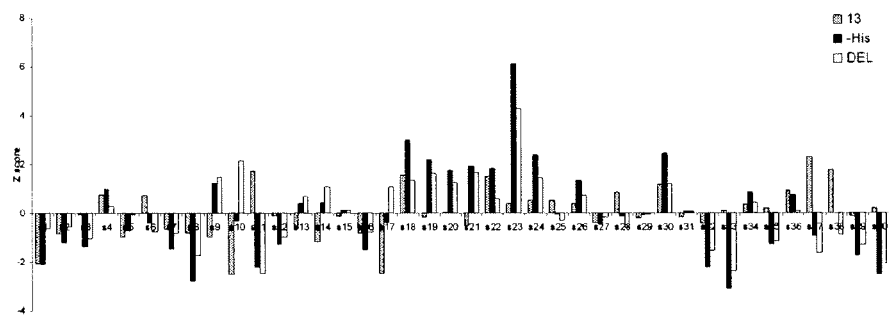
FIG. 2 shows a representative sample of a z-score calculation-based graph with a radioprotector at S11 position. Clearly shows an increase in +13 growth (z-score value of +1.71), significantly reduced –His growth (z-score value of –2.23), and a significantly reduced DEL recombination event (z-score value of –2.46) when compared to controls.
Figure 3:
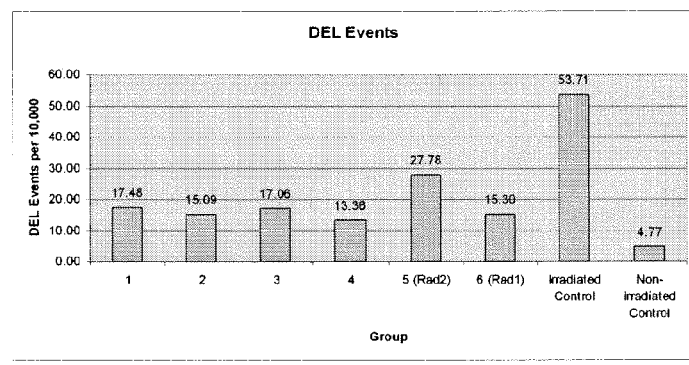
FIG. 3 shows the number of DEL events per 10,000 cells in RS112 *Saccharomyces cerevisiae* cells following a 2000Gy irradiation. Each bar represents the number of DEL recombination events from an averaged 3 plating experiments.
Figure 4:
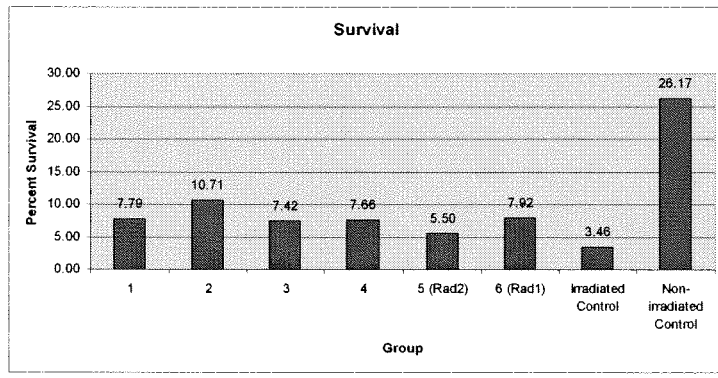
FIG. 4 shows the percent survival of RS112 *Saccharomyces cerevisiae* cells following a 2000Gy irradiation. The survival differences are statistically significant: Compounds 1-4 and 6 (Yel1 (Rad1)) had p-values <0.01 and Compound 5 (Yel2 (Rad2)) had with p<0.05.
Figure 5:
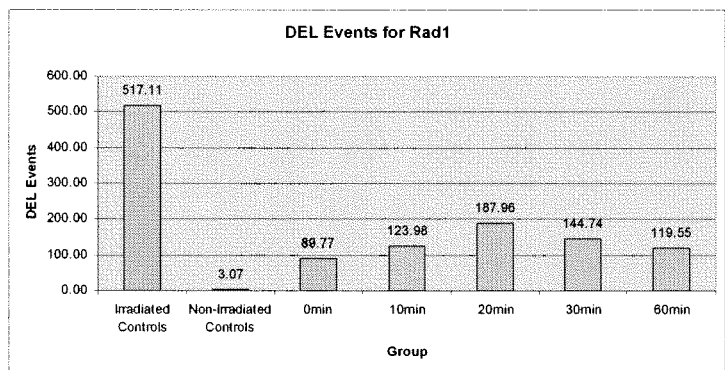
FIG. 5 shows a representative graph of mitigation activity affecting DEL frequency of Yel1 (Rad1) in RS112 cells. Mitigation activity for all compounds has been observed up to 60 minutes after 2000Gy irradiation. Each bar represents the number of DEL recombination events from an average of 3 experiments.
Figure 6:
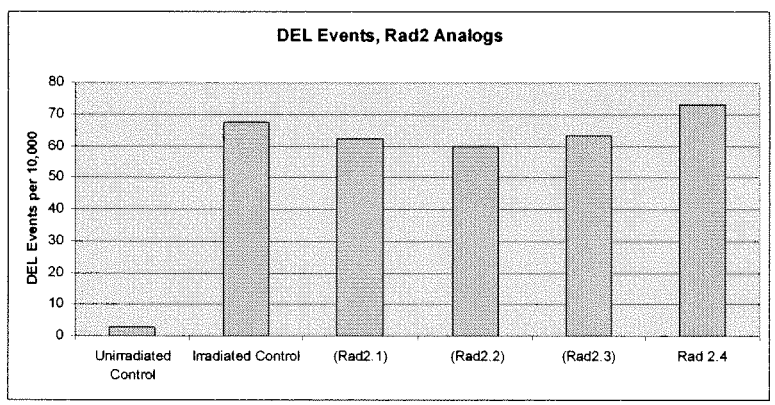
FIG. 6 shows a representative graph of radioprotection activity in Yel2 (Rad2) analogues after a 2000Gy irradiation. Each bar represents the number of DEL recombination events from an average of 3 experiments.
Figure 7:
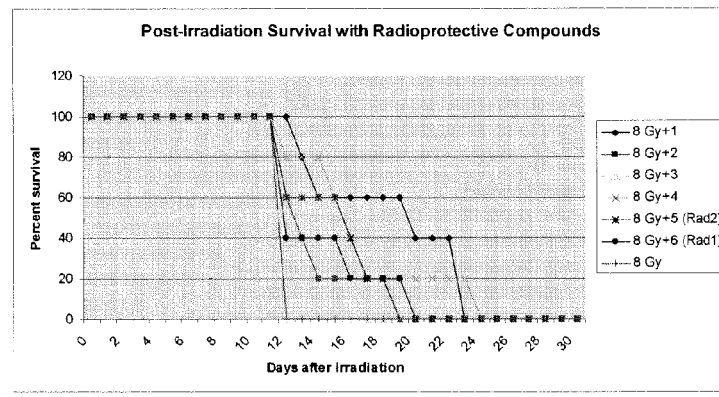
FIG. 7 shows a noticeable difference in survival between 8 Gy control group and groups 1, 4, and 5 (Yel2 (Rad2)). The statistical significance, however, falls just a little short of p<0.05, at p=0.058 14 days post irradiation for groups 1 and 5 (Yel2 (Rad2)), but is significant for group 4 at p=0.016.
Figure 8:
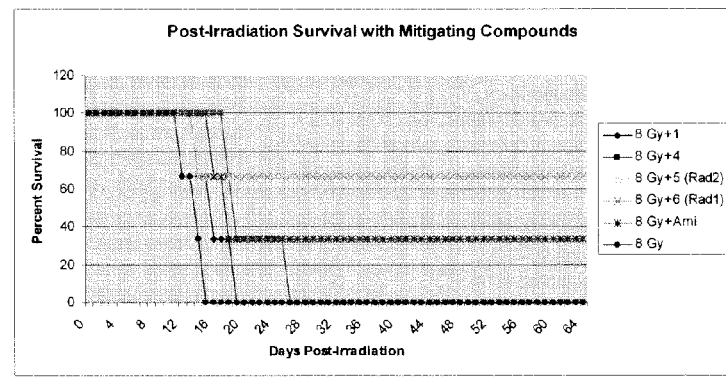
FIG. 8 shows an observable difference between groups 5 (Yel2 (Rad2)) and 6 (Yel1 (Rad1)) and the rest of the study groups—here 67% of the mice in the group have survived past 30 days. 33% of mice treated with Amifostine™ are still alive. The results are encouraging but due to the small number of mice, an in-depth statistical analysis is unavailable.
Figure 9:
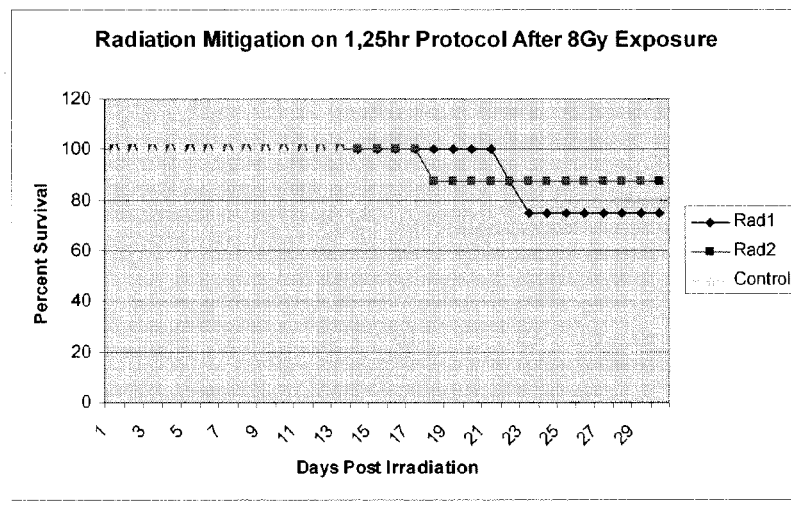
FIG. 9 shows the results of tests where 8 Male C3H mice for each condition were irradiated at 8Gy (LD100/30) and then treated sc twice: 1 hr and 25 hrs post exposure with compounds Yel1 (Rad1) and Yel2 (Rad2) at a concentration of 75 mg/Kg in PBS carrier, controls were injected with the carrier only. Yel2 (Rad2) treatment has a p-value of 0.0117, Yel1 (Rad1) treatment p-value=0.0455.

In one aspect of the present invention, it is provided a compound, which is effective for mitigating tissue damage and lethality induced by an agent. The compound can be a synthetic compound or a natural product in a substantially purified form. The compound also includes a pharmaceutically acceptable salt thereof, a prodrug thereof, a hydrate thereof, a solvate thereof, or a polymorphic crystal thereof.

In some embodiments of the compound, the compound has a general structure of

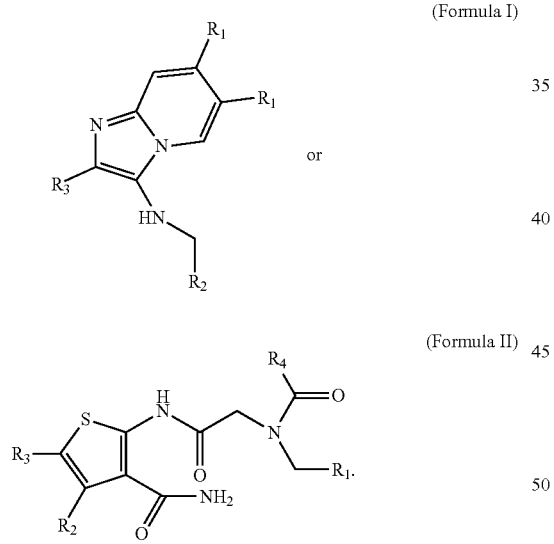

(Formula I)

or (Formula II)

In Formula I, each $R_1$, $R_2$ and $R_3$ are independently hydrogen, straight chain or branched C1-C20 alkyl, alkenyl, or alkynyl, which is substituted or unsubstituted, cyclo alkyl, cyclo alkenyl, heterocyclic alkyl, or heterocyclic alkenyl, which is substituted or unsubstituted, phenyl, substituted phenyl, aryl, substituted aryl, amino, amido, F, Cl, Br, I, nitro, hydroxyl, thiol, alkylthio, selenol, alkylselenyl, silyl, siloxy, boryl, carboxylic acid, sulfonyl, —SO$_4$H, alkoxy, or acyl groups along with a list of the following exemplary substitutions:

Each $R_1$ independently=one or more of the following NH$_2$, OH, OMe, Me, H, CH$_2$OH, BH$_2$, SMe, $R_2$ =

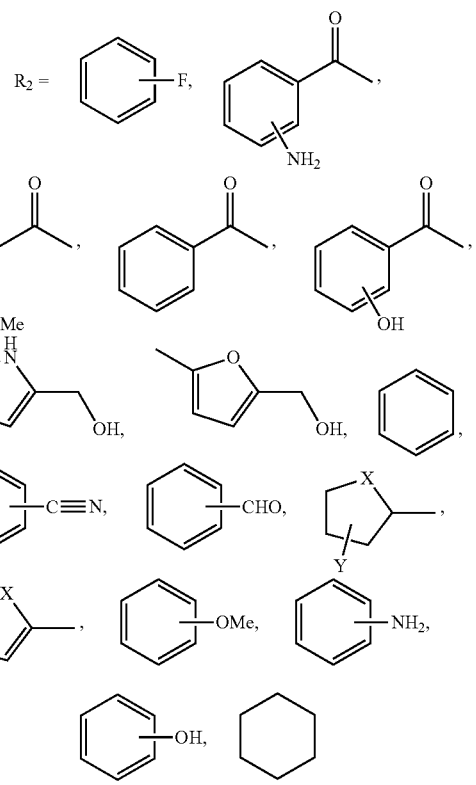

X=S, HN, O, BH, CH$_2$;
Y=NH$_2$, OH, OMe, Me, H, CH$_2$OH, BH$_2$, SeMe, SMe $R_3$ =

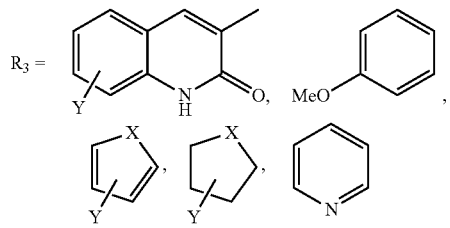

X=S, HN, O, BH, CH$_2$
Y=NH$_2$, OH, OMe, Me, H, CH$_2$OH, BH$_2$, SeMe, SMe

In Formula II, $R_1$, $R_2$, $R_3$, and $R_4$ are independently hydrogen, straight chain or branched C1-C20 alkyl, alkenyl, or alkynyl, which is substituted or unsubstituted, cyclo alkyl, cyclo alkenyl, heterocyclic alkyl, or heterocyclic alkenyl, which is substituted or unsubstituted, phenyl, substituted phenyl, aryl, substituted aryl, amino, amido, F, Cl, Br, I, nitro, hydroxyl, thiol, alkylthio, selenol, alkylselenyl, silyl, siloxy, boryl, carboxylic acid, sulfonyl, —SO$_4$H, alkoxy, or acyl groups along with a list of the following exemplary substitutions:

$R_1$=$R_4$ and are:

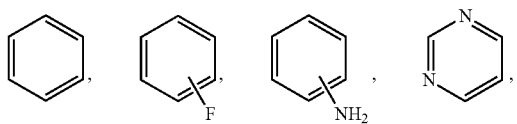

-continued

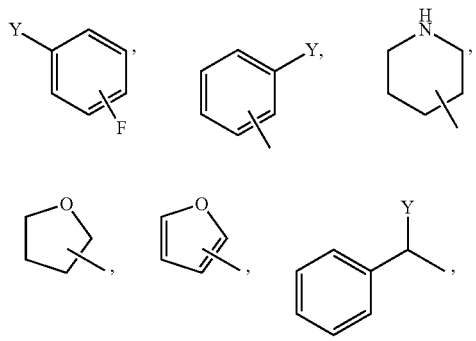

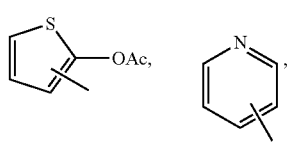

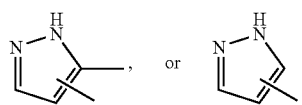

Y=CH₃, OH; and
$R_2=R_3=$ and are CH₃, OH, O, SH, H, NH₂, or

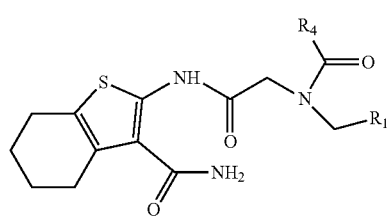

In some embodiments of the compound, the compounds of formula I can have a Tanimoto coefficient 0.7 or above, based on compound of formula IA:

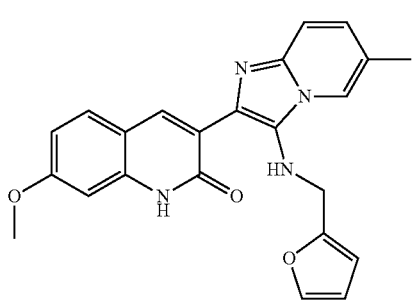 [SMILES: COc1ccc2cc(-c3nc4ccc(C)cn4c3NCc3ccco3)c(=O)[nH]c2c1]

(Formula IA, also described below as Yel002 or Rad2), and compounds of formula II can have a Tanimoto coefficient Tanimoto coefficient 0.7 or above, based on the compound of formula IIA or formula IIB:

[Formula IIA structure]

(Formula IIA, also described below as Rad1 or Yel001)

[Formula IIB structure]

(Formula IIB, also described below as CJ010).

In some embodiments, in Formula I:
$R_1$ is a short chain alkyl, such as methyl, ethyl, an alkenyl, or phenyl;
$R_2$ is an alkyl, alkenyl, or aryl, such as phenyl, or 2-furanyl; and

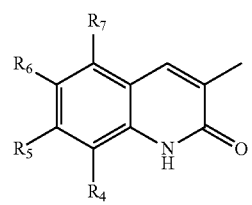

$R_3$ is a group having formula III, Formula III, where $R_4$, $R_5$, $R_6$, and $R_7$ are independently H, short chain alkyl such as methyl, ethyl, propyl, isopropyl, n-butyl, or t-butyl, phenyl, short chain alkoxy, such as methoxy, or ethoxy, phenoxy, halo (F, Cl, Br, or I), or amino groups. In some embodiments, in formula II₁, $R_4$, $R_6$, and $R_7$ are hydrogen, and $R_5$ is methoxy.

In some embodiments of the compound, in the compound of Formulae I, $R_1$, $R_2$, $R_3$, $R_4$, $R_5$, $R_6$, and $R_7$ are selected such that compound of Formula IA is specifically excluded from the definition of the compound of Formula I.

In some embodiments, the compound is an analogue of Formula IA selected from Formulae IB-IH:

Formula IB
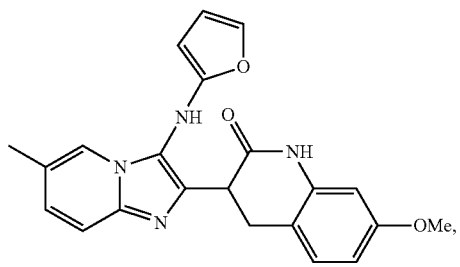

Formula IC
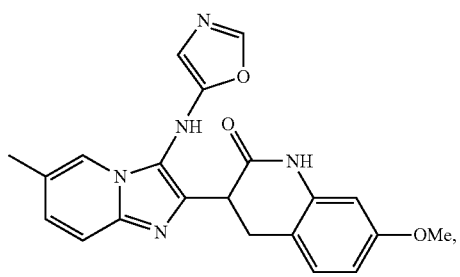

Formula ID
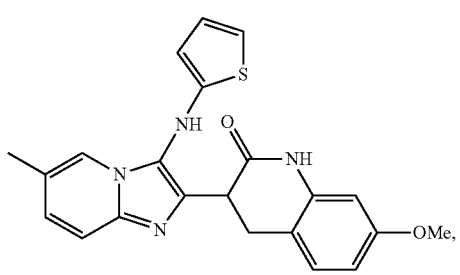

Formula IE
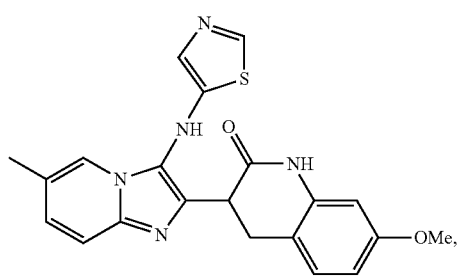

Formula IF
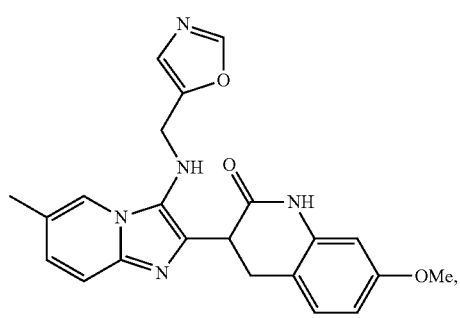

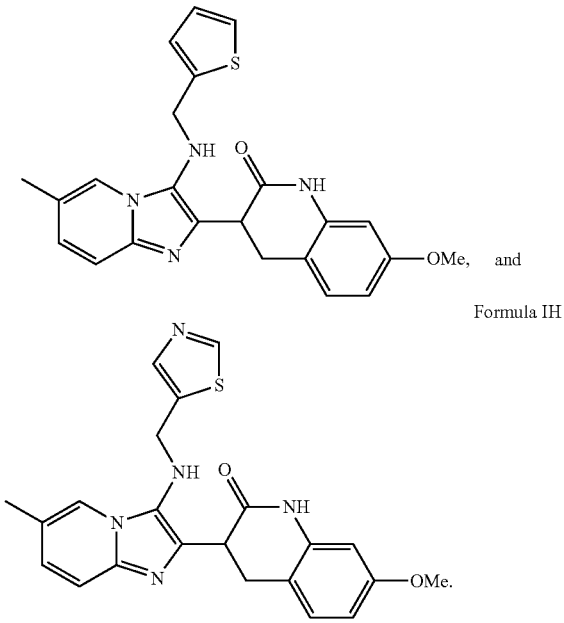

Formula IG (top) and Formula IH (bottom).

In some embodiments of the compound, in the compound of Formulae II, $R_1$, $R_2$, $R_3$, and are selected such that compound of Formula IIA is specifically excluded from the definition of the compound of Formula II.

In some embodiments of the compound, it is a natural product in a substantially purified form. In some embodiments, the compound has a Formula I or Formula II, both defined above. As used herein, the term "substantially purified" refers to a purity of about 70% or higher, about 80% or higher, about 90% or higher, about 95% or higher, about 99% or higher.

Further, the compounds of the present invention include hydrates thereof, various pharmaceutically acceptable solvates thereof, and polymorphic crystals thereof.

A compound disclosed herein can be isolated from a natural source or prepared according to established methodology in the art of organic synthesis. General methods of synthesizing the compound can be found in, e.g., Stuart Warren and Paul Wyatt, Workbook for Organic Synthesis: The Disconnection Approach, second Edition, Wiley, 2010. Exemplary methods of making the compound is provided in the general section of the Examples, described below.

In another aspect of the present invention, it is provided a composition, which composition comprising a compound of the various embodiments disclosed herein. The composition comprises the compound in an amount effective for mitigating tissue damage or lethality induced by an agent. In some embodiments, the composition includes a compound in an effective amount for a condition selected from conditions related to radiation-induced lethality, conditions related to radiation-induced genotoxicity and cytotoxicity, conditions related to radiation-induced damage to healthy tissues during radiation therapy, conditions related to radiation-induced persistent genetic instability, conditions related to ultraviolet (UV) radiation-induced damage, conditions related to damage induced by chemical carcinogens, radiation-induced cancer, spontaneous cancer, or aging.

In some embodiments of the composition, the composition can further optionally include at least one other therapeutic agent.

In some embodiments of the composition, the composition of various embodiments disclosed herein further comprises an excipient.

In some embodiments of the composition, the composition of various embodiments disclosed herein further comprises a pharmaceutically acceptable carrier.

The composition of various embodiments disclosed herein can be formulated into a formulation for local delivery or systemic delivery. In some embodiments, the composition is formulated into a formulation for oral administration, injection, topical administration, implant, or pulmonary administration.

The composition of various embodiments disclosed herein can be a therapeutic composition, a cosmetic composition, or a dietary supplement.

In a further aspect of the present invention, it is provided a method of screening for a compound effective as a radiation protective/mitigating agent. The method comprises:

generating a screening system capable of screening a compound against radiation-induced cell killing, genetic instability, or both; and subject a compound to the screening, and identifying a compound as radiation protective if the compound significantly reduces radiation induced cell killing or genetic instability as compared to a control.

In some embodiments of the method, the compound has a structure of Formula I or Formula II.

In a further aspect of the present invention, it is provided a method of preparing a compound. The method comprises preparing a compound according to the various embodiments disclosed above.

In a further aspect of the present invention, it is provided a method of preparing a composition. The method comprises providing a compound which is effective for mitigating tissue damage and lethality induced by an agent, and forming the composition of the various embodiments disclosed herein. The compound is as in the various embodiments disclosed herein.

In a further aspect of the present invention, it is provided a method of treating, preventing, or ameliorating a condition. The method comprises administering to a subject a compound or a composition according to the various embodiments of disclosed herein.

In some embodiments of the method, the condition is selected from conditions related to radiation-induced lethality, conditions related to radiation-induced genotoxic and cytotoxicity, conditions related to radiation-induced damage to healthy tissues during radiation therapy, conditions related to radiation-induced persistent genetic instability, conditions related to ultraviolet (UV) radiation-induced damage, conditions related to damage induced by chemical carcinogens, radiation-induced cancer, spontaneous cancer, or aging.

In a still further aspect of the present invention, it is provided a method of radiation therapy. The method comprises:

administering to a subject a compound of invention, and
administering to the subject a radiation;

wherein the subject has a medical condition capable of being treated or ameliorated by radiation.

In some embodiments, the compound is included in a composition.

In some embodiments, the composition further includes an optional second agent.

In some embodiments of the method, the medical condition is cancer, e.g., skin cancer or leukemia.

As used herein, the term "pharmacologically acceptable salt" is not specifically limited as far as it can be used in medicaments. Examples of a salt that the compound of the present invention forms with a base include the following: salts thereof with inorganic bases such as sodium, potassium, magnesium, calcium, and aluminum; salts thereof with organic bases such as methylamine, ethylamine and ethanolamine; salts thereof with basic amino acids such as lysine and ornithine; and ammonium salt. The salts may be acid addition salts, which are specifically exemplified by acid addition salts with the following: mineral acids such as hydrochloric acid, hydrobromic acid, hydroiodic acid, sulfuric acid, nitric acid, and phosphoric acid:organic acids such as formic acid, acetic acid, propionic acid, oxalic acid, malonic acid, succinic acid, fumaric acid, maleic acid, lactic acid, malic acid, tartaric acid, citric acid, methanesulfonic acid, and ethanesulfonic acid; acidic amino acids such as aspartic acid and glutamic acid.

As used herein, the term "prodrug" shall mean a precursor (forerunner) of a drug. A prodrug must undergo chemical conversion by metabolic processes before becoming an active pharmacological agent.

As used herein, the term "significantly reduces" shall mean a reduction of cell killing or genetic instability by a percentage of 5% or higher, 10% or higher, 25% or higher, 50% or higher, 75% or higher, 100% or higher, 200% or higher, 500% or higher, or 1000% or higher.

As used herein, the terms "Yel1", "Yel001", and "Rad1" are used interchangeably.

As used herein, the terms "Yel2", "Yel002", and "Rad2" are used interchangeably.

Tanimoto coefficient has been widely used in the art of design and preparation of compounds with similar physical, chemical, and pharmacological properties (see, Ajay Kumar, et al., Computational Approach to Investigate Similarity in Natural Products Using Tanimoto Coefficient and Euclidean Distance, The IUP Journal of Information Technology, Vol. 6, No. 1, pp. 16-23, March 2010; Gen Kawamura, Shigeto Seno, Yoichi Takenaka and Hideo Matsuda: "A Combination Method of the Tanimoto Coefficient and Proximity Measure of Random Forest for Compound Activity Prediction", IPSJ Digital Courier, Vol. 4, pp. 238-249. (2008)).

Formulations

The composition disclosed herein can be formulated into various formulations. The composition can be formulated for systemic or local delivery of the radiation protective compound. For example, such formulations include, e.g., liquid, solid, or semi-solid formulations for various mode of administration, e.g., oral administration, subcutaneous injection, intravenous injection, topical administration, or implant.

The compositions can be formed into a formulation suitable for a desired mode administration. In some embodiments, the composition can include a pharmaceutically acceptable carrier. The content of the compound disclosed herein in the composition according to the present invention may range, but is not limited to, preferably from 0.001 to 20 wt. %, more preferably from 0.01 to 15 wt. %, most preferably from 0.05 to 10 wt. %.

Formulations can be made suitable for different routes of administration, for example, liquids for intravenous administration, topical administration via application to the surface of the diseased site, or mucosal application to cavities of the nose, mouth, eye, rectum, vagina or bronchopulmonary; solid dosage forms that may dissolve in the mouth or be inhaled through the broncopulmonary; and semisolids that may be applied to cavity surfaces of the nose, mouth, eye, rectum, or vagina.

Examples of the carrier employed in the composition disclosed herein can include any desired carriers generally contained in drugs, fibers, polymeric materials and the like. Concerning pharmaceutical compositions, illustrative of such desired carriers are excipients, coloring matters, taste or smell corrigents, binders, disintegrators, coating materials, stabilizers, pH regulators, sugar-coating materials, emulsifiers, dispersants, and solubilizers. Especially for external dermal preparations, illustrative examples can include hydrocarbons such as liquid paraffin and vaseline, esters such as spermaceti and bees wax, triglycerides such as olive oil and beef tallow, higher alcohols such as cetanol and oleyl alcohol, fatty acids such as stearic acid and oleic acid, polyhydric alcohols such as propylene glycol and glycerin, nonionic surfactants, anionic surfactants, cationic surfactants, and thickeners. For clothing and plastics, illustrative examples can include plasticizers, crosslinking agents, coloring matters, antioxidants, and ultraviolet absorbers.

In some embodiments, an aqueous preparation or formulation of the composition disclosed herein may contain buffers, surfactants, humectants, preservatives, flavorings, stabilizers (including antioxidants) colorants, and other additives used in preparations administered into the oral cavity.

In some embodiments, liquid compositions preferably should have a pH value ranging from 2 to 10, preferably 3.5 to 9, most preferably 4 to 8. A preparation having a pH of less than 4 would be likely to cause a stinging sensation. Furthermore, the preparations having a higher pH are often unpleasant to use. The active agents need not be in solution to be effective. The active agents may be present wholly or in part as suspensions in aqueous solutions used as carriers to provide liquid compositions. The preparations are buffered as necessary to provide the appropriate pH.

Appropriate buffer systems include citric acid-citrate salts, acetic acid-acetate salts, and benzoic acid-benzoic salt systems. However, any buffer system commonly used for preparing medicinal compositions would be appropriate. While the vehicle used generally is primarily water, other vehicles may be present such as alcohols, glycols (polyethylene glycol or polypropylene glycol are examples), glycerin, and the like may be used to solubilize the active agents. Surfactants may include anionic, nonionic, amphoteric and cationic surfactants which are known in the art as appropriate ingredients for mouthwashes.

Liquid formulations may contain additional components to improve the effectiveness of the product. For example, component(s) may be added to increase viscosity to provide improved retention on the surfaces of the oral cavity. Suitable viscosity increasing agents include carboxyalkyl, hydroxyalkyl, and hydroxyalkyl alkyl celluloses, xanthan gum, carageenan, alginates, pectins, guar gum, polyvinylpyrolidone, and gellan gums. Gellan gums are preferred since aqueous solutions containing certain gellan gums may be prepared so that they will experience an increase in viscosity upon contact with electrolytes.

Some examples of the formulations of the composition disclosed herein include, for example, solid formulations such as tablets, capsules, granules, pills, troches, powders or suppositories, or liquid formulations such as syrups, elixirs, suspensions or injections, as well as aerosols, eye drops, ointments, ophthalmic ointments, emulsions, creams, liniments or lotions. These formulations may be prepared in accordance with conventional methods commonly used in the field of drug formulations.

In some embodiments, various additives which are commonly used in the drug formulation field, can be used. Such additives include, for example, saccharides such as lactose or glucose, a starch such as corn, wheat or rice, a vegetable oil such as soybean oil, peanuts oil or sesame oil, a fatty acid such as stearic acid, an inorganic salt such as magnesium metasilicate aluminate or anhydrous calcium phosphate, a synthetic polymer such as polyvinylpyrrolidone or polyalkylene glycol, a fatty acid salt such as calcium stearate or magnesium stearate, an alcohol such as stearyl alcohol or benzyl alcohol, a synthetic cellulose derivative such as methyl cellulose, carboxymethyl cellulose, ethyl cellulose or hydroxy-propylmethyl cellulose, or others such as water, gelatin, talc and gum arabic.

Further, in the case of a liquid formulation, it may be in such a form that at the time of use, it is dissolved or suspended in water or in other suitable medium. Especially when administration is carried out by e.g. intramuscular injection, intravenous injection or subcutaneous injection, a suitable medium for such an injection may, for example, be distilled water for injection, a hydrochloric acid lidocaine aqueous solution (for intramuscular injection), physiological saline, an aqueous glucose solution, ethanol, liquid for intravenous injection (such as an aqueous solution of citric acid and sodium citrate) or an electrolyte solution (for intravenous drip and intravenous injection), or a mixed solution thereof. Further, a buffer or a preservative may be added.

In some embodiments, for delivery into a cell, the composition disclosed herein can be formulated into liposomal preparations (e.g., liposomal suspensions or particles). Liposomal suspensions (including liposomes targeted to infected cells with monoclonal antibodies to viral antigens) are also preferred as pharmaceutically acceptable carriers. Methods for encapsulation or incorporation of compounds into liposomes are described by Cozzani, I.; Jori, G.; Bertoloni, G.; Milanesi, C.; Sicuro, T. Chem. Biol. Interact. 53, 131-143 (1985) and by Joni, G.; Tomio, L.; Reddi, E.; Rossi, E. Br. J. Cancer 48, 307-309 (1983). These may also be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound is then introduced into the container. The container is then swirled by hand to free lipid material from the sides of the container and to disperse lipid aggregates, thereby forming the liposomal suspension.

Other methods for encapsulating compounds within liposomes and targeting areas of the body are described by Sicuro, T.; Scarcelli, V.; Vigna, M. F.; Cozzani, I. Med. Biol. Environ. 15(1), 67-70 (1987) and Joni, G.; Reddi, E.; Cozzani, I.; Tornio, L. Br. J. Cancer, 53(5), 615-21 (1986).

These formulations may contain usually from 0.001 to 100 wt %, preferably from 0.005 to 100 wt %, of the active ingredient in the case of the above-mentioned solid formulations, and may contain from 0.05 to 10 wt %, preferably from 1 to 5 wt %, in the case of other formulations.

A practically preferred dose of the compositions disclosed herein varies depending upon the type of the compound used, the type of the composition blended, the sex, age, weight, diseased degree and the particular section to be treated of the patient, but it is usually from 0.1 to 150 mg/kg in the case of oral administration and from 0.01 to 150 mg/kg in the case of parenteral administration, per adult per day. The number of times of administration varies depending upon the administration method and the symptom, but it is preferred to carry out the administration from one to five times per day.

As used herein, the terms "formulation" and "preparation" are used interchangeably.

As used herein, the term "radiation" refers to radiation by radioactive elements, which are well known by an oncology practitioner as well as radiation of a magnetic wave, e.g., alpha radiation, beta radiation, gamma radiation, neutron radiation, x-ray radiation, ultraviolet radiation. X-rays are a very common form of radiation used in radiotherapy. Gamma rays are another form of photons used in radiotherapy. Gamma rays can be produced spontaneously as certain elements (such as radium, uranium, and cobalt 60), which release radiation as they decompose, or decay. Each element decays at a specific rate and can give off energy in the form of gamma rays and other particles. Typically x-rays and gamma rays have the same general effect on cancer cells. In some embodiments, the radiation refers to any radiation in therapy (e.g., cancer therapy). In some embodiments, the radiation refers to high LET radiation.

As used herein, the term "radioactive element" refers to particle radiation by radioactive particles. Such radioactive particles can be any radioisotopes commonly used in cancer treatment or emitted from a nuclear power plant. Examples of radioactive particles include, e.g., carbon-13, nitrogen-15, oxygen-18, etc. Such radioactive particles are well documented and within the general knowledge in the art (see, e.g., Joao Jose Pedroso de Lima, *Eur. J. Phys.* 19(6) 485 (1998); Ian (lore-Lacy (Lead Author); World Nuclear Association (Content Partner); Cutler J. Cleveland (Topic Editor);. 2009. "Radioisotopes in medicine." In: Encyclopedia of Earth. Eds. Cutler J. Cleveland (Washington, D.C.: Environmental Information Coalition, National Council for Science and the Environment).

Other Therapeutic Agents

In some embodiments, the compound disclosed herein can combine with one or more other therapeutic agents so as to provide combinatorial treatment. Such other therapeutic agents that can be combined with the compound disclosed herein include, but are not limited to, Amifostine, free radical scavengers, growth factors, immune modulators, anti-apoptotic agents, capture agents et cetera.

In some embodiments, the compound disclosed herein can be used with NAC (N-acetylamine)

Method of Use

The compound or composition disclosed herein can be used for treating or ameliorating various conditions pertaining to radiation-induced tissue damage or genetic stability. For example, the compound or composition disclosed herein can be used for mitigation of radiation-induced lethality, radiation-induced genotoxic and cytotoxicity, radiation-induced damage to healthy tissues during radiation therapy, radiation-induced persistent genetic instability, ultraviolet (UV) radiation-induced damage, or damage induced by chemical carcinogens. In some embodiments, the compound or composition disclosed herein can be used for reduction of radiation-induced cancer or the frequency of spontaneous cancer, e.g., leukemia. In further embodiments, the compound or composition disclosed herein can be used for modulation or mitigating genetic instabilities associated with aging.

The invention method of use generally comprises administering to a subject (e.g., a human being) a compound or a composition disclosed herein. Such administering can be local administration or systemic administration, which administering can be achieved by, for example, oral administration, subcutaneous injection, intravenous injection, topical administration, or implant.

Examples of conditions related to radiation-induced lethality include, but are not limited to, early radiation lethality: death occurring within a few weeks following an intense radiation exposure, at very high doses (>100Gy) at 24-48 hrs death occurs most likely due to the collapse of the neurologic and cardiovascular systems (cerebrovascular syndrome); at intermediate dose of 5-12Gy death occurs within weeks due to severe bloody diarrhea as a result of obliteration of gastrointestinal mucosa (gastrointestinal syndrome); at lower doses of 2.5-5 Gy death occurs at weeks to months after exposure due to the failure of the blood-forming organs (bone-marrow death or hematopoietic syndrome). Death can also occur much later due to radiation-induced cancer.

Examples of conditions related to radiation-induced genotoxic and cytotoxicity include, but are not limited to, direct and indirect DNA damage: single strand breaks, double strand breaks, oxidation of bases; cytotoxicity: cell death by necrosis, apoptosis, or an entrance into senescence and thus loss of function.

Examples of conditions related to radiation-induced damage to healthy tissues during radiation therapy include, but are not limited to nausea and vomiting after irradiation of the abdominal area, fatigue, somnolence after cranial irradiation, acute edema and erythema that results from radiation-induced inflammation after vascular leakage, radiation fibrosis, Telangiectasia, loss of hair and sebaceous glands, xerostemia as a result of loss of the mucosal cells in the oral cavity; additionally, aplasia and pancytopenia in the bone marrow, acute and chronic hepatitis in the liver, obstruction, perforation, and fistula in the intestine, perforation, hemorrhaging, and ulcer in the stomach, infarction and necrosis in the brain/spinal cord, pericarditis and pancarditis, acute and chronic pneuomonitis, acute and chronic nephrosclerosis, ulceration and stenosis in the rectum, sterilization in the ovaries and testes, growth arrest and dwarfism in growing cartilage in children, blindness if retina and cornea are irradiated, cataracts in lens, hypothyroidism, sensory otitis, muscular atrophy and fibrosis, artery and vein sclerosis, etc.

Examples of conditions related to radiation-induced persistent genetic instability include, but are not limited to, loss of genetic integrity as a result of DNA damages that were incorrectly repaired, mutation, chromosomal aberrations that lead to higher instances of carcinogenesis, reproductive abnormalities, teratogenesis, higher frequencies of spontaneous cancers in the offspring of irradiated individuals.

Examples of conditions related to ultraviolet (UV) radiation-induced damage include, but are not limited to, cataracts, melanoma, carcinoma, premature aging, pinguecula, etc.

Examples of conditions related to damage induced by chemical carcinogens include, but are not limited to, hemangiosarcoma (Arsenic exposure), mesothelioma (Asbestos exposure), leukemia and Hodgkin lymphoma (Benzene exposure), lung cancer (cigarette smoke: active, second, and side stream).

Examples of radiation-induced cancer include, but are not limited to, skin cancer, acute and chronic myeloid leukemia, thyroid cancer, breast and lung cancer, bone cancer, etc.

Examples of spontaneous cancer include, but are not limited to, leukemia, lung, breast, colon, and pancreatic cancers.

EXAMPLES

The embodiments of the present invention are illustrated by the following set forth examples. All parameters and data shall not be construed to limit the scope of the embodiments of the invention.

General Procedures, Methods, and Materials

A phenotypic in vitro screen is employed from which structural analogs from a library of the compounds of formulae IA (Yel 1) and IIA (Yel 2) (Targeted Library) are subjected to screening for radiation protective candidates that are efficacious in vivo.

A. Mice and Rat

All survival studies performed in vivo in this application have been C3H mice. Radiation-induced leukemia studies conducted at AFRR1 involved C57BL6 mice. The survival studies were performed using Gamma-ray emitter (Cesium 137 source) for the total exposure dose of 8 Gy (LD100/30) in the radioprotection and radiomitigation studies.

Radiomitigation Studies.

Radiomitigation studies were conduced by pre-treating C3H mice with the compounds of interest at as concentration of 75 mg/kg and at 24 hrs and 1 hr before an 8 Gy exposure. On a 5×24 mitigation treatment protocol mice were first lethally irradiated with 8 Gy and 24 hrs later received the first subcutaneous injection with the compound suspension with subsequent injections at 48, 72, 96, and 120 hrs. The concentration of the compound in the suspension was 75 mg/kg carrier with either 1N saline or phosphate buffer solution (PBS). On the 1.25 protocol the mice were lethally irradiated with 8 Gy and then treated at 1 hr and 25 hrs following exposure (FIG. 7-11, 21).

Leukemia Studies.

Figure 17:
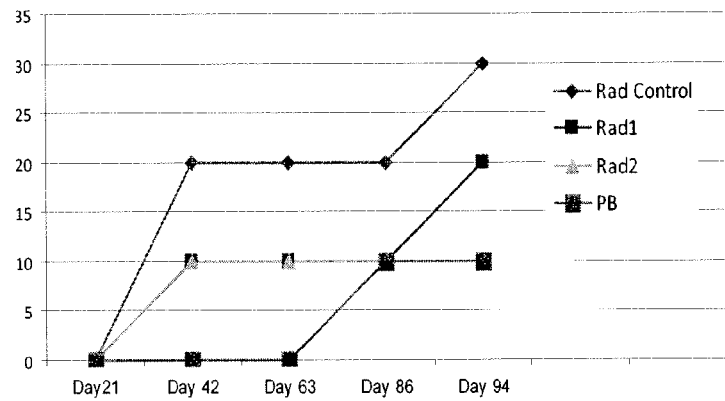
FIG. 17 shows the results of the test of Yel002 (Rad2) and Yel001 (Rad1) in the radiation-induced leukemia model in vivo. At Day 94, 30% of the irradiated controls have developed leukemia; treatment with Yel002 has reduced the frequency to 10% and Yel001 to 20%.
Figure 18:
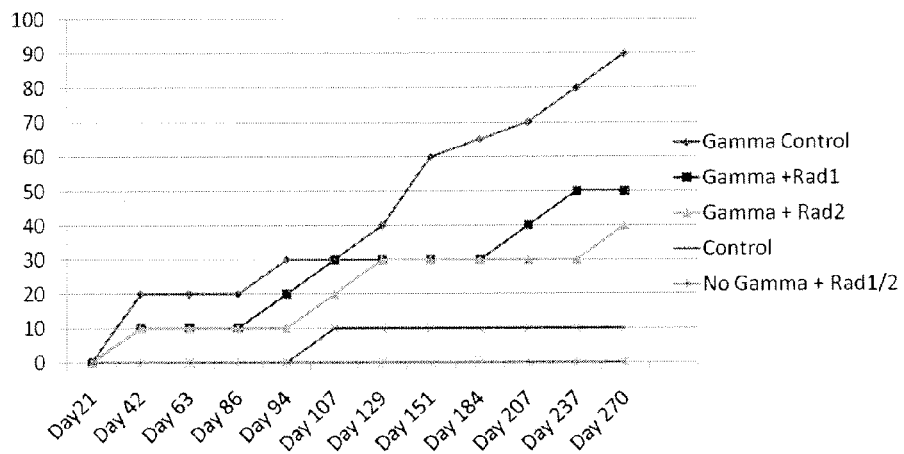
FIG. 18 shows that Yel001 (Rad2) and Yel002 (Rad1) are effective for reducing the frequency of radiation induced and spontaneous cancer.

Leukemia studies were conducted by irradiating C57BL6 mice with sub lethal IR dose and transplanting bone marrow. Treatment then began with 5 doses at 25 mg/kg suspensions injected at 24, 48, 72, 96, and 120 hrs (FIGS. 17 and 18).

B. Targeted Library—Analog Inclusion

Analogues within at least 70% or greater similarity as defined by the Tanimoto rule of similarity are believed to have similar results as the aforementioned compounds in this application. Analogs from the library sets with the similarity scores of 70% or better have shown activity in preliminary studies: for example compounds from the UCLA chemical screening library such as 5346033 (99% similarity to Yel002), 5346021 (98% similarity to Yel002), 5346069 (96% similarity to Yel002), 5346081 (94% similarity to Yel002), 5346037 (89% similarity to Yel002), 5345724 (82% similarity to Yel002), and a de novo synthesized Yel002 fragment 2-[2-(Benzoyl-benzyl-amino)-acetylamino]-4,5-dimethyl-thiophene-3-carboxylic acid amide; 6156077 (97% similarity to Yel001), 6156259 (90% similarity to Yel001), 6156426 (87% similarity to Yel001), 6156076 (86% similarity to Yel001), 6156817 (79% similarity to Yel001), 6154166 (76% similarity to Yel001), and 6156829 (75% similarity to Yel001). Other structures within this limitation (Tanimoto rule of similarity as described and positive in DEL/Survival assay) are included. The DEL Assay, which is further described below, has established itself not only as a effective tool in carcinogenic activity detection but also as an effective methodology in establishing DNA protective properties against insults such as free radicals and ionizing radiation (see, e.g., Sobol, Z., et al., Mutation Research/Fundamental and Molecular Mechanisms of Mutagenesis, 2008. 638(1-2): p. 83-89, Hafer, K., Rivina, L., Schiestl, R H. *Yeast DEL assay detects protection against radiation induced cytotoxicity and genotoxicity—adaptation of a microtiter plate version, Radiation Research,* 2010, 174(6):719-26)). Thus, the DEL Assay is a reliable tool for the prediction of genotoxic and cytotoxic modulating agents. These agents also include, but are not limited to, ionizing radiation, UV radiation, environmental carcinogenesis, genetic instability, etc.

Lipinski Properties.

Lipinski rule of five can be used to determine how likely a compound can become a drug, which is described in C. A. Lipinski; et al., (2001). "Experimental and computational approaches to estimate solubility and permeability in drug discovery and development settings". *Adv Drug Del Rev* 46: 3-26). Lipinski properties of Yel002 (Formula IA) and Yel001 (Formula IIA) are described below:

Yel001

| Lipinski Properties | |
|---|---|
| Molecular weight | 439.502 g/mol |
| log P | 5.00876 |
| H-bond donors | 2 |
| H-bond acceptors | 5 |
| Lipinski Rule of 5 | One violation |
| Formula | $C_{23}H_{22}FN_3O_3S$ |
| $pK_a$ | −0.960924 |
| Exact mass | 439.137 g/mol |
| Composition | C (62.85%), H (5.05%), F (4.32%), N (9.56%), O (10.92%), S (7.3%) |

| Lipinski Properties | |
|---|---|
| Molecular weight | 400.430 g/mol |
| log P | 3.53972 |
| H-bond donors | 2 |
| H-bond acceptors | 5 |
| Lipinski Rule of 5 | Satisfied |
| Formula | $C_{23}H_{20}N_4O_3$ |
| $pK_a$ | 7.22848 |
| Exact mass | 400.154 g/mol |
| Composition | C (68.99%), H (5.03%), N (13.99%), O (11.99%) |

Identification of Lead Radiation Mitigators

A. Determining the Effects of Structural Analogues of Lead Radiation Mitigators in Vitro.

The compounds are identified as being effective for mitigating radiation-induced cell damage (cytotoxicity) as well as DNA damage (genotoxicity) in low- and high-dose radiation exposure.

Compounds in the Targeted Library are selected as a development candidate using the Tanimoto coefficient. For Yel1 we have identified 210 analogues at 70% similarity, 50 analogues at 85% similarity, and 24 analogues at 90% similarity; for Yel2 we found 217 analogues at 70%, 43 analogues at 85%, and 25 analogues at 90%. Tests were performed which showed that these compounds had similar mitigation activity in vitro.

Radioprotection Activity of Structural Analogues of Lead Compounds In Vitro.

DEL Assays

All DEL assays utilize the established methodology of "recombination" (deletion of the interruption segment and consequent end joining of the adjacent sequences) of a disrupted histidine gene that renders yeast cells exposed to radiation capable of growing on media lacking this amino acid. In the classical DEL assay radiation sensitive RS112 strain of *S. cerevisiae* is added to the compounds of interest suspended in complete media, incubated for 2 hrs, and irradiated at 2000Gy. The cells are then plated onto full (+13) and lacking histidine (−His) agar plates. After incubation the colonies are scored and recombination events are calculated. The efficacy of the compound is evaluated as a reduced fraction of DEL recombinations in comparison to that of irradiated controls without treatment. Radioprotectors decrease the frequency of such recombination frequencies after radiation exposure.

High Throughput DEL Screen.

In the high throughput adaptation of the assay the compounds are suspended in liquid full media (+13) and in media lacking histidine (−His) on a microtiter plate.

Following the re-suspension RS112 *S. cerevisiae* cells, synchronized at the synthesis stage, are added. The plate is then irradiated at 2000Gy and a color indicator is added (Promega CellTiter 96® AQ$_{ueous}$ Non-Radioactive Cell Proliferation Assay). After 16 hrs of incubation absorption is measured at 490 nm and the DEL recombination frequencies are calculated. As a part of the analogue screen, target microtiter plates are created with all 410 analogues, which are subjected to screen in this high throughput format for radioprotection activity. We have observed that the compounds with radioprotection activity also tend to have mitigation properties; compounds having high radioprotection activity are selected for further mitigation studies.

Identifying False Positives:

All analogues of Yel1 and Yel2 displaying high radioprotection activity will be subjected to the classical DEL Assay to identify potential false positives. Only those compounds that pass this rigorous test are tested in the DEL Mitigation Assay.

B. Establishing Mitigation Activity in Structural Analogues of Lead Compounds In Vitro.

The mitigation protocol is based on the same DEL assay principle of recombination of the disrupted HIS3 gene that renders the cells capable of synthesizing its own histidine following radiation exposure. To establish mitigation properties of the compounds in question, the classical DEL protocol is modified as follows: first the RS112 cells are irradiated with 2000Gy and then the treatments are administered at 0 min, 10 min, 20 min, 30 min, and 60 min, incubated for 2 hrs, and plated on +13 and −His agar plates. The efficacy of the compounds is scored the same way as in the classical DEL protocol. Yel1 and Yel2 analogues that are efficacious in the HTS and classical DEL assay are analyzed for mitigation activity using this modified DEL protocol.

C. Synthesizing Compounds with Mitigation Activity for Studies In Vivo.

Compounds showing mitigation activity in the DEL assays are organized according to their similarity to the Yel1 and Yel2 and Lipinski rule satisfaction—compounds most similar to parent compounds and complete Lipinski rule fulfillment are synthesized. Compounds from the libraries are either commercially available or synthesized according to established methodologies. General methods of synthesizing the compound can be found in, e.g., Stuart Warren and Paul Wyatt, Workbook for Organic Synthesis: The Disconnection Approach, second Edition, Wiley, 2010.

Example 1

Identification of Radiation Mitigators

Summary

We identified novel radiation mitigators from chemical libraries, which are inducers of DNA repair and are general anticancer agents since spontaneous cancers are due to the same mechanisms as radiation causes, namely oxidative damage and strand breaks.

All the hits from the yeast assay also protected human cells from radiation toxicity and prolonged the life of mice after radiation. Two of the chemicals turned out to be powerful radiation mitigators in that 67% of animals survived a lethal dose of radiation when the chemicals were given one hour and again 24 hours after radiation. The reason for this result can be several folds. One is that by screening against radiation induced genetic instability in addition to toxicity, it is more likely to select for chemicals that induce DNA repair which repairs damage leading to increased survival as well as reduced genetic instability. This is supported by our finding that nucleotide excision repair is involved in the adaptive response to radiation (data not shown).

Furthermore, delayed effects of radiation include persistent genetic instability and mutations which may actually be involved in the delayed toxicity. We have previously shown that radiation induces such persistent genetic instability (Brennan, R. J. and R. H. Schiestl, Radiat Res, 2001. 155(6): p. 768-77) with the very same assay that we used for screening for radioprotectors. Thus, our rationale that a reduction of such genetic instability would produce a good radiation mitigator was verified. Furthermore, genetic instability is involved in carcinogenesis and our assay is shown to be a good predictor of carcinogenesis by chemicals (see, e.g., Carls, N. and R. H. Schiestl, Mutation Research, 1994. 320 (4): p. 293-303) and mice genetically predisposed to a high frequency of cancer also show elevated frequencies of the same DNA deletions that we used as a screen in yeast (see, e.g., Aubrecht, J., et al., Carcinogenesis, 1999. 20(12): p. 2229-36; and Reliene, R., et al., Adv Genet, 2007. 58: p. 67-87). Accordingly, the radiation mitigators of invention disclosed herein can also reduce radiation-induced carcinogenesis.

The Yeast DEL Assay

A plasmid with an internal fragment of the HIS3 gene, which is responsible for histidine synthesis in yeast, without which cells cannot survive in media lacking histidine, has been integrated at the HIS3 locus, yielding an integrative disruption of the HIS3 gene (Schiestl, R. H., et al., Genetics, 1988. 119(2): p. 237-47). This resulted in two copies of the HIS3 gene, each having one terminal deletion. The construct reverts to HIS3+ by recombination between the two his3 deletion alleles which is, in 99% of the cases, associated with the deletion of the entire 6 kilobasepairs of DNA comprising the integrated plasmid. This system has thus been termed as the deletion (DEL) assay (Schiestl, R. H., Nature, 1989. 337 (6204): p. 285-8) (see FIG. 1).

DEL recombination is inducible by a variety of *Salmonella* assay negative carcinogens which are not detectable with the *Salmonella* assay or with other short-term tests (see, e.g., Carls, N. and R. H. Schiestl, Mutation Research, 1994. 320 (4): p. 293-303). The data obtained with the DEL assay to date are very promising.

In summary, these data show that 14 *Salmonella*-positive carcinogens and 22 *Salmonella*-negative carcinogens induced DEL recombination. From a total of 47 chemicals the *Salmonella* assay detected 16 correctly and the DEL assay detected 40 correctly (see, e.g., Carls, N. and R. H. Schiestl, Mutation Research, 1994. 320(4): p. 293-303). 31 of the agents tested were chosen because they are false negatives or false positives (not correctly identified) in the *Salmonella* assay. Only 34% of these chemicals were correctly identified with the *Salmonella* assay, compared with 85% correctly identified with the DEL assay. This establishes a higher correlation with carcinogenesis for the DEL assay compared to the *Salmonella* assay that screens for point mutations.

Double-Strand Breaks Induce DNA Deletions.

DEL recombination is very well induced by double-stranded DNA breaks. Expression in yeast cells of I-SceI, a site specific endonuclease with a single restriction site between the two copies of the gene duplication resulted in deletion frequency of almost 100% (Galli, A. and R. H. Schiestl, Genetics, 1998. 149(3): p. 1235-50). This observation is also supported by the fact that agents which produce DNA strand breaks, such as X-rays and oxidative mutagens (Brennan, R. J., et al., *Oxidative mutagens induce intrac hromosomal recombination in yeast*. Mutation Research, 1994. 308 (2): p. 159-67), are positive in the yeast DEL assay.

N-Acetyl Cysteine Protects Against Ionizing Radiation-Induced DNA Damage but not Against Cell Killing in Yeast and Mammals (Data not Shown).

In this study, we examined the role of N-acetyl-L-cysteine (NAC), a clinically proven safe agent, for it's ability to protect against γ-ray-induced DNA strand breaks and/or DNA deletions in yeast and mammals. In the yeast *S. cerevisiae*, DNA deletions were scored by reversion to histidine prototrophy. Human lymphoblastoid cells were examined for the frequency of γ-H2AX foci formation, indicative of DNA double strand break formation. DNA strand breaks were also measured in mouse peripheral blood by the alkaline comet assay. In yeast, NAC reduced the frequency of IR-induced DNA deletions. However, NAC did not protect against cell death. NAC also reduced γ-H2AX foci formation in human lymphoblastoid cells but had no protective effect in the colony survival assay. NAC administration via drinking water fully protected against DNA strand breaks in mice whole-body irradiated with 1 Gy. NAC treatment in the absence of irradiation was not genotoxic. These data suggest that, given the safety and efficacy of NAC in humans, NAC can be useful in radiation therapy to prevent radiation-mediated genotoxicity, but does not interfere with efficient cancer cell killing.

Cell Cycle Dependence of Ionizing Radiation-Induced DNA Deletions and Antioxidant Radioprotection in *Saccharomyces Cerevisiae* (Data not Shown).

In this study we used the DEL assay to measure gamma-ray induced DNA deletions throughout different phases of yeast culture growth. While yeast survival only differed by as much as two fold throughout the yeast growth phase, proliferating cells in lag and early exponential growth phases were ten-fold more sensitive to ionizing radiation-induced DNA deletions than cells in stationary growth. Radiation-induced DNA deletion potential was found to directly correlate with the fraction of cells in $S/G_2$ phases. The ability of antioxidants L-ascorbic acid and DMSO to protect against radiation-induced DNA deletions was also measured within the different phases of yeast culture growth. Yeast cells in lag and early exponential growth phases were protected by antioxidant treatment, whereas non-dividing cells in stationary phase could not be protected against DNA deletion induction. This knowledge was used for the screening of radioprotectors.

Yeast High Throughput DEL Screen:

Yeast high throughput DEL screen is described above. Roughly 16,000 compounds from the small molecule libraries have been screened in a DEL High Throughput format to yield 36 lead compounds. These 36 leads had a statistically significant reduction in the radiation-induced DNA recombination (genotoxicity protection) and an increased survival (cytotoxicity protection) in the RS112 strain of *Saccharomyces cerevisiae*.

These 36 leads were then tested in the same high throughput microtiter format to yield 6 "hit" compounds.

DEL Plating Assay:

The 6 hits were then re-confirmed in the more sensitive "gold standard" classical DEL Plating Assay. All 6 hits (1, 2, 3, 4, 5 (Yel2), and 6 (Yel1)) again have shown radioprotector characteristics with genotoxicity and cytotoxicity protection qualities.

DEL Plating Assay for Mitigation of Radiation Damage:

Six confirmed hits were also tested for radioprotection with the compounds being presented to irradiated cells at different time points following irradiation exposure. The DEL Plating Assay was used with a radiation sensitive *Saccharomyces cerevisiae* RS112 strain.

Summary of Studies on Data Convergence and Application of Collaborative Drug Discovery (CDD) Software:

Similarity and Substructure Analysis.

Briefly, the CDD™ platform was utilized to perform similarity and substructure searches in silico to analyze and compare the structure of all hits. For each hit, a similarity search was performed where the entire library is ranked according to its structural similarity to the referenced hit based upon the Tanimoto coefficient. Data possessing a coefficient lower than 0.7 were excluded. Consequently, hits within the library of similar structure as well as non hits of similar structure were identified. Non hit compounds possessing strong similarity were re-screened to address the possibility of false negatives. For classes of compounds possessing similar structural elements and positive hits, a substructure analysis was performed to determine the minimal elements that persist within all hit compounds in that family. Thus, SAR data was obtained for both Yel1 and Yel1 (data not shown). Using the system to compare our data with experiments on mammalian cell lines, it revealed an overlap with Compound 6 (Yel1) (data not shown). Compound 6 (Yel1) in a Therapy Bioluminescence Assay has shown a significant increase in survival (130% as compared to that of controls) following irradiation (data not shown). Furthermore, all other compounds also showed some effect, although to a lesser degree (data not shown). In addition, using the CDD database application we were able to assess the relative toxicity of the hit compounds using the Drug Only Bioluminescence (data not shown). None of the compounds have shown significant decrease in survival following the exposure to the compound.

In addition, using the similarity and substructure analysis we have identified 10 analogues that showed activity in high throughput screen but were not selected for further analysis at the time when Yel1 and Yel2 were tested. We have tested these analogues with the classical DEL assay and saw radioprotection activity in 5 of these. These studies demonstrated that there is a correlation between structure and activity.

Toxicity Experiments in C3H Mice:

Having seen no adverse effects of the chemicals alone on mammalian cell models we performed a preliminary toxicity study on a group of C3H mice. Exposures at 150 mg/kg, 75 mg/kg and 5 mg/kg of Yel1 and Yel2 in mice did not show any adverse physiological nor behavioral adverse effects 120 days following the injections. In a pilot reproductive toxicity study, 12, week old female mice were paired up with 6 week old male mice and checked daily for the presence of a characteristic "plug" in the female vaginal canal as an indication of mating. As soon as the mating has occurred, males were removed and the females were treated weekly with 75 mg/kg s.c. throughout the gestation period and until the pups were weaned off (8 week treatment course). After weaning, treatment of the offspring was initiated at the same 75 mg/kg s.c. weekly dose. Controls were injected s.c. on the same schedule with the carrier (1N saline). Five treated and five control females gave birth to the same average number of pups per litter (n=6) without any detectable toxicities to the other. 3 litters of each treated and control groups survived to continue the study. No pathologies, toxicities nor adverse effects were observed. There are no developmental or teratogenic deficiencies in mice, average weights (21 g) are the same in both groups also.

Radioprotection Experiments in C3H Mice:

Exposure of C3H mice to 8Gy (LD100/30) in the presence of the hit compounds (75 mg/kg) has shown an increase in survival for Compounds 1, 4, and 5 (Yel2). Only the results for Compound 4 are significant at Day 14 post irradiation. Irradiated controls died on Day 13 while most of the treated mice survived to Day 18, and mice in group 4 and 1 have survived to Day 24. The limitation of this study was the number of mice in each group due to the small quantities of the commercially available compounds.

Mitigation Experiments in C3H Mice:

C3H mice in the mitigation experiment were irradiated with 8Gy and then injected with 75 mg/kg 1 hr post exposure and then again 25 hrs post exposure. Once again, the study was limited by the availability of the compound. However, the results are still striking: 67% of mice have survived the LD100/30 irradiation dose with Compounds 5 (Yel2) and 6 (Yel1), and 33% of mice have survived after treatment with Amifostine™. All of the surviving mice have survived past Day 90 and have not exhibited any pathologies. The control mice have died on Day 15 post irradiation.

Example 2

Studies on Mitigation Efficacy of Yel1 and Yel1

The mitigation efficacy of Yel1 and Yel2 was tested within the actual therapeutic window: we have exposed radiation-sensitive C3H mice to 8Gy of ionizing radiation (LD100/30) and then treated them five times at 24, 48, 72, 96, and 120 hrs with Yel1, Yel1 (75 mg/Kg) and PBS carrier. Yel2 has demonstrated a remarkable mitigation property: 100% survival (p-value=0.0209) at an LD100/30. Yel1 also showed efficacy (See FIG. 9). The same dose of 8Gy caused 100% death in the control in about 15 other experiments.

Figure 10:
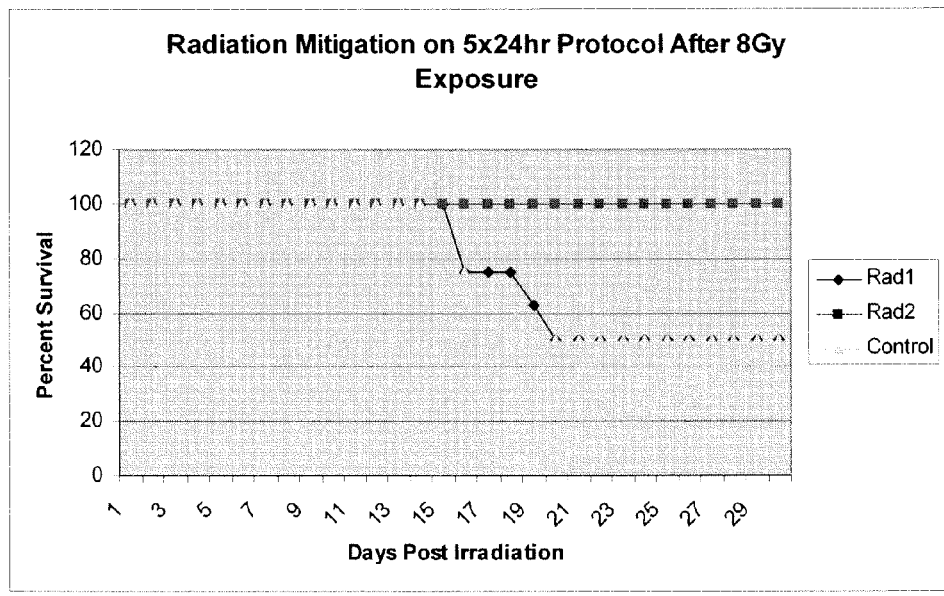
FIG. 10 shows the results of tests where 8 Male C3H mice for each condition were irradiated at 8Gy (LD100/30) and then treated sc five times at 24, 48, 72, 96, and 120 hrs post exposure with compounds Yel1 (Rad1) and Yel2 (Rad2) at a concentration of 75 mg/Kg in PBS carrier, controls were injected with the carrier only. Yel2 (Rad2) treatment has a p-value of 0.0209, Yel1 (Rad1) treatment.

In addition, we have also replicated our original results with a 1.25 hr post irradiation treatment: both Yel1 and Yel2 show activity on this therapeutic schedule (Yel1 p-value=0.0455 and Yel2 p-value=0.0117) (See FIG. 10). This treatment protocol has application for first responders arriving at the site of the radiological incident and persons likely to receive high radiation doses through prolonged exposures.

Examples 3-11

Studies on Mitigating Effects of Compounds on Radiation-Induced Conditions

Radiation protective compounds Yel001 (Formula IIA) and Yel002 (Formula IA) were subjected to various tests on their respective effects as radiation mitigator. The results are described below.

Example 3

Mitigation of Radiation-Induced Lethality

Compounds Yel001 and Yel002 have shown mitigation of radiation-induced lethality on two treatment protocols: an "early intervention" protocol with the first treatment administered at 1 hr and the second at 25 hrs post exposure (1.25) and a "late intervention" protocol where five doses are administered every 24 hrs with the first one being at 24 hrs after irradiation (5×24). The 1.25 treatment protocol has application for first responders arriving at the site of the radiological incident and for persons likely to receive high radiation doses through prolonged exposures. The 5×24 treatment protocol has application as a therapy for accidental exposures such as a "dirty bomb" detonation or a reactor leakage where large populations are at risk of being exposed to lethal doses of radiation and where medical attention is likely to be provided hours later.

Figures 11A, 11B:
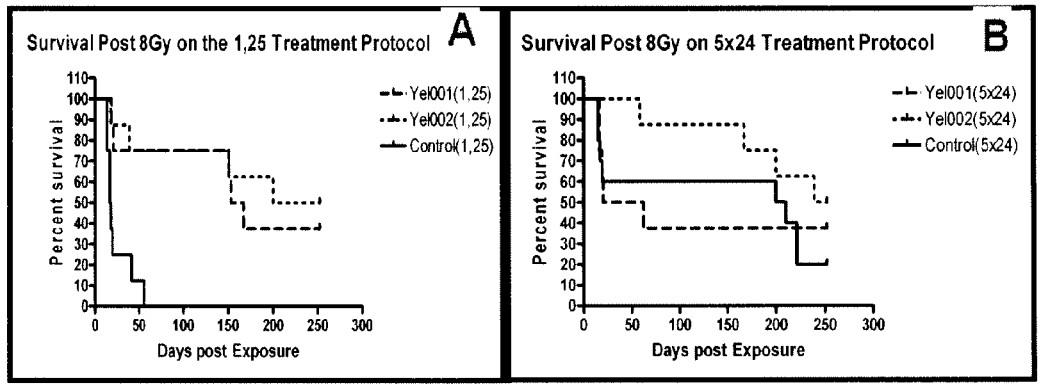
FIGS. 11A and 11B shows results of tests where Male C3H mice for each condition were irradiated at 8Gy (LD100/30) and then treated sc either twice at 1 hr and 25 hrs post exposure with compounds Yel001 and Yel002 or five times at 24, 48, 72, 96, and 120 hrs at a concentration of 75 mg/kg in PBS carrier. Controls were injected with the carrier only.

To test the efficacy of the compounds in both therapeutic scenarios, radiation-sensitive C3H mice were exposed to 8Gy of ionizing radiation (LD100/30) and then treated subcutaneously (SQ) five times at 24, 48, 72, 96, and 120 hrs with Yel001 or Yel002 (75 mg/kg) and PBS carrier (FIGS. 11A and 11B) or treated 1 hr and 25 hrs after the exposure with the same dose as the 5×24 groups. Without any signs of toxicity or advert effects Yel002 demonstrated remarkable mitigation activity: 100% survival at an LD100/30 within the standard 30-day experimental period on the 5×24 treatment regimen; on the 1.25 schedule 88% of mice survived within the same timeframe (FIGS. 11A and 11B). Yel001 did not exhibit significant efficacy on the 5×24 experiment within the day period; however, Yel001 did show therapeutic benefit on the 1.25 treatment regimen (FIG. 11A). Following surviving mice beyond the standard 30 day experimental window (+292 days) on both protocols 40% of animals are still alive in the Yel002 groups and 30% in the Yel001 groups.

Again, in FIGS. 11A and 11B, at the standard cut off point of 30-day we have observed 100% survival with Yel002 on the 5×24 protocol, and 88% on the 1.25 schedule. However, at 252 days post irradiation, the pattern of radiation mitigation appears to be similar on both treatment protocols with higher percentage of survivors treated with Yel002 (40%) than with Yel001 (30%). All treated survivors are healthy without any indication of pathologies. Untreated survivors are showing signs of latent radiation-induced gastrointestinal damage.

Figure 12:
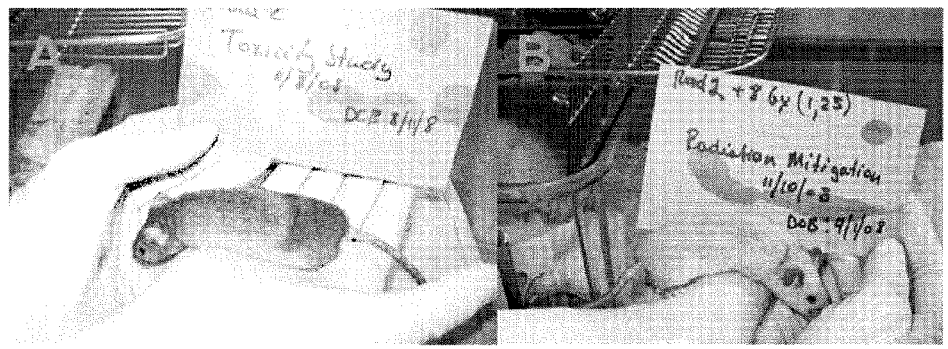
FIG. 12 shows photos of the coat changes in mice surviving lethal doses of radiation (8 Gy, LD100/30). Panel A: Day 265 following i.p. injections with Yel002. Panel B: Day 260 post irradiation at 8 Gy and subsequent treatment with Yel002 at 1 hr and 25 hr.
Figure 13:
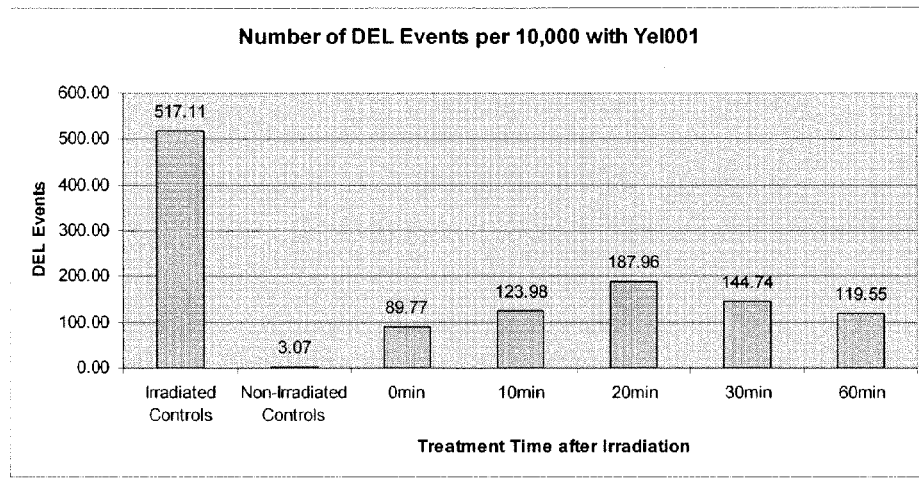
FIG. 13 shows reduction of DEL events with Yel001 treatment following a 2000Gy irradiation on RS112 cells. At all five time points there is a significant reduction of genetic instability as expressed by the reduction of the gene reversion frequencies (p-value <0.05).
Figure 14:
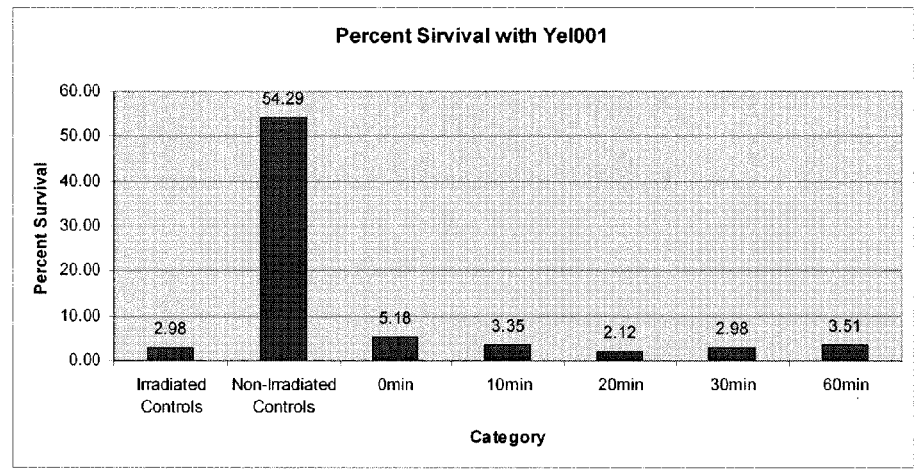
FIG. 14 shows mitigation of radiation cytotoxicity has been observed with the addition of Yel001 at various time points. Difference in survival is only significant at the 60 min time point for both compounds.
Figure 15:
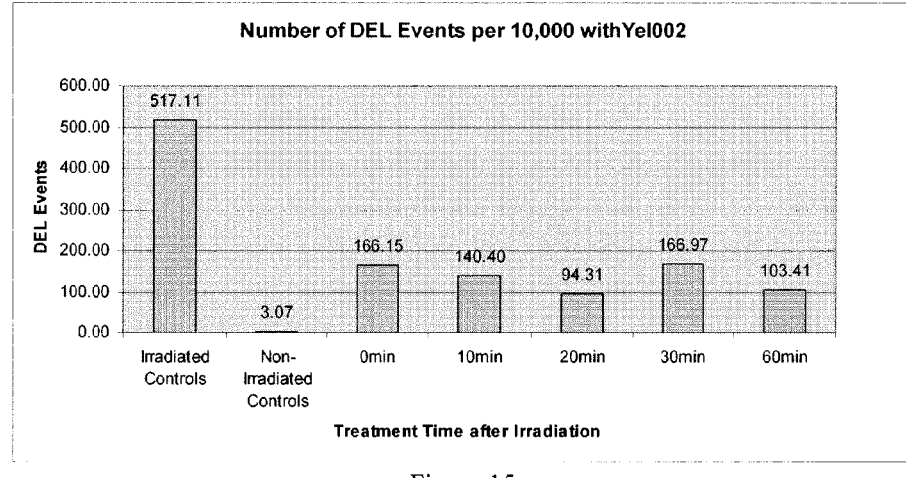
FIG. 15 shows reduction of DEL events with Yel002 treatment following a 2000Gy irradiation on RS112 cells. At all five time points there is a significant reduction of genetic instability as expressed by the reduction of the gene reversion frequencies (p-value <0.05).
Figure 16:
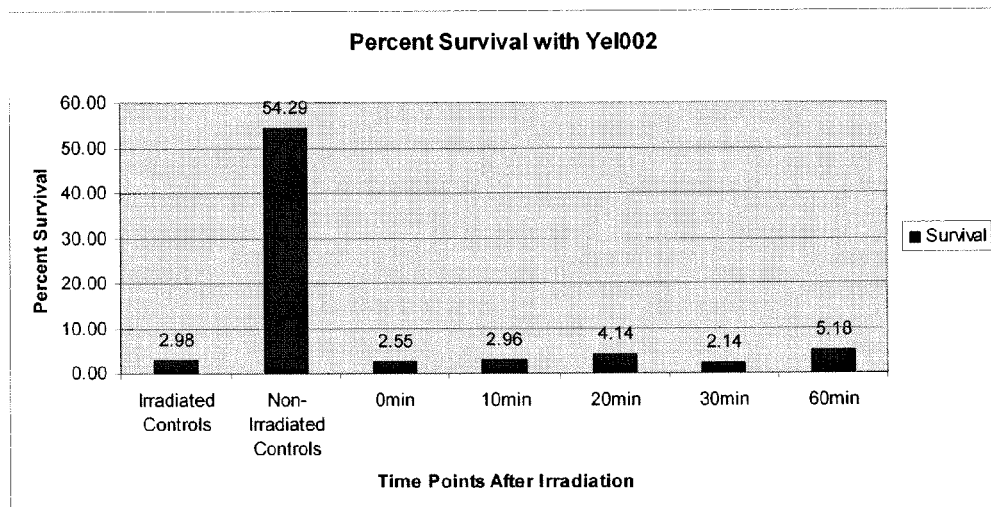
FIG. 16 shows mitigation of radiation cytotoxicity has been observed with the addition of Yel002 at various time points. Difference in survival is only significant at the 60 min time point for both compounds.

FIG. 12 shows the photos of mice treated with radiation mitigator Yel002 prior to radiation or post radiation.

The surviving mice were kept alive after the 30-day period to investigate our belief that those agents that mitigate radiation-induced cell death and DNA damage in yeast can possess similar qualities in in-vivo models. Survivors of lethal ionizing radiation exposures tend not to exhibit long-term genetic instability as assessed by the frequency of spontaneous tumors (none were observed) and damage to the gastrointestinal epithelium. Additionally, we have observed that in the long run the survival frequencies are identical between the two therapeutic schedules possibly indicating that the therapeutic window extends beyond the first hours following exposure. This result is of therapeutic significance when translated into real life scenarios: there are possibilities of radiation mitigation intervention for large and hard to reach populations.

Example 4

Mitigation of Radiation-Induced Genotoxicity and Cytotoxicity

We utilized the yeast DEL assay to test Yel001 and Yel002 compounds for radiation-mitigation properties.

The general DEL Assay is described above. In this example, DEL assay is a genetic construct in the *Saccharomyces cerevisiae* RS112 strain where a plasmid with an internal fragment of the HIS3 gene has been integrated at the HIS3 locus, yielding an integrative disruption of the HIS3 gene. This resulted in two copies of the HIS3 gene, each having one terminal deletion. The construct reverts to HIS3+ by recombination between the two his3 deletion alleles which is, in 99% of the cases, associated with the deletion of the entire 6 kilobasepairs of DNA comprising the integrated plasmid. DEL events are inducible with a variety of DNA-assaulting agents: radiation, smoking, UV exposure, 92% of the known carcinogens, etc.

RS112 cells irradiated with 2000Gy show an induction of the deletion frequencies (DEL events) and roughly a 90% killing. Addition of Yel001 and Yel002 to the irradiated cells at various time points following the exposure and a 24-hour incubation has resulted in decreased DEL frequencies and increased survival fractions (FIGS. 13-16).

Example 5

Mitigation of Radiation-Induced Damage to Healthy Tissues During Radiation Therapy During radiation therapy—purposeful exposure to Gamma-, X-ray, proton, heavy ion, and neutron radiation—with the goal to destroy malignant neoplastic formations (tumors), not only the cancerous masses are affected, normal tissues are exposed to high doses of radiation with malignant consequences: direct—radiation burns, tissue necrosis, and indirect—apoptosis induced with the by-standard effect, acute immune response, etc.

Administration of Yel001 and Yel002 following radiation treatments would provide an effective therapeutic tool in the reduction of radiation-associated damage in healthy tissues without compromising the effectiveness of the radiation treatment on the malignant tissues. The option of having a radiation mitigator aimed at healthy tissue protection would provide the opportunity to either increase the total or fraction dose of radiation or completely revise the accepted fractionated radiation treatments as one of the main concerns in such therapeutic schemes is the sparing of normal tissue (late responding healthy tissue).

Radiation mitigation properties of Yel001/Yel002 as observed in the above described experiment indicate the potential of these compounds to also mitigate damage to the healthy tissues during radiation therapies.

Example 6

Mitigation of Radiation-Induced Persistent Genetic Instability

Studies described above not only measure mitigation of radiation induced geno- and cytotoxicities in vitro but they also assess the compounds' ability to reduce long-term genetic instability associated with high-dose radiation exposures (gamma, UV, etc). Incubation of cells with Yel001 or Yel002 24 hours following irradiation and subsequent treatment allows for the irradiated cells to divide at least 12 times before being plated. Chromatin damage associated with radiation exposures shows up only after the cells have either committed or attempted to divide; thus, the cells treated with Yel001 and Yel002 will demonstrate reduced DEL frequencies indicative of the reduction of radiation-induced long-term genetic instability.

Reduction in long-term genetic instability is observed in the test animals that have survived a 100% lethal dose of 8Gy. These animals do not exhibit increased cancer frequencies nor any other abnormalities expected after such high-dose exposures.

Reduction of persistent genetic instability associated with gamma radiation as seen in vitro and in vivo models can be translated into other scenarios of persistent genetic instability mitigation: exposures to particulate radiation, ultraviolet radiation, genetic mutations (p53, ATM, etc).

Example 7

Reduction of Radiation-Induced Cancer

Yel001 and Yel002 Treatment Inhibits Development of Radiation-Induced Leukemia.

DBA/2 Mice (15/group) were irradiated with $^{60}$Co (3.5 Gy, 0.6 Gy/min) to induce leukemia. One group received no drug, another group of mice were injected s.c. with Yel001 or Yel002 (25 mg/kg) with 5 injections for 5 days. Leukemogenesis was monitored for 90 days. Blood was drawn at days −1, 21, 42, and 63 to monitor for leukemia every 21 days to monitor for leukemia development using WBCs and differentials.

Results are shown in FIG. 17 where Yel001 and Yel002 increased latency to leukemia development. The first development of leukemia in irradiated mice (no drug) occurred within 42 days post-radiation; similarly Yel001 and Yel002 mice demonstrated their first leukemia's at day 42 as well. At day 94 30% of the mice exhibited leukemia while only 20% and 10% of mice treated with Yel001 and Yel002 respectively exhibited leukemia. It is important to note that this is at $\frac{1}{3}^{rd}$ the original dosage of 75 mg/kg. Furthermore, at a later time point (Day 270, FIG. 18) the irradiated population had 90% leukemia, treatment with Yel1 and Yel2 reduced the leukemia frequency to 50% and 40% respectively. The spontaneous frequency is decreased from 10% to 0% (FIG. 18).

Leukemia Model.

This leukemia model takes advantage of non-targeted radiation effects, which are important to the carcinogenic process. This model has a shorter latency period to gamma radiation-induced leukemia (latency to 50% leukemic population: 107 days) than other murine leukemia models such as CBA mouse (399 days: 50% leukemic population). DBA/2 mice were irradiated with 3.5 Gy ($^{60}$Co 0.60 Gy/min) and then injected intravenously with (5×10$^6$) FDC-P1 cells. Animals were then monitored 5×/weekly for 10 weeks-post-injection and then daily after 10 weeks-post-injection until leukemia development and/or euthanasia. After the animal has been determined to be leukemic using hematological parameters, it is euthanized and a necropsy is conducted to definitively determine a conclusive diagnosis of leukemia. Control animals not developing leukemia are assessed at 270 days post experiment initiation. At that time they are euthanized and necropsied. To monitor leukemia development, blood samples are obtained from day −1 and every 21 days until euthanasia.

Figure 22:
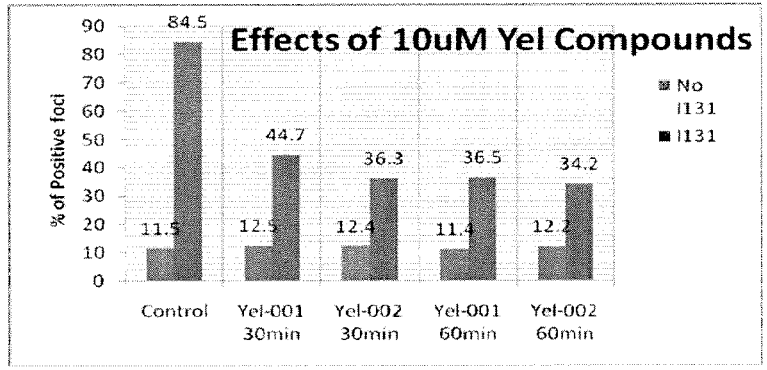
FIG. 22 shows the results of tests mitigating $^{131}$I-induced double stand breaks in human thyroid cell.

Additionally, administration of Yel compounds up to an hour after exposure to radioactive Iodine-131 (I131), a major fallout product after nuclear explosions ultimately causing thyroid cancers, has significantly reduced the number of double strand breaks (DSB) from 84.5% to an average of 36% (FIG. 22). This carries major implications in terms of mitigation of radiation-associated damage implying that the administration of Yel compounds leads to a decrease in DNA lesions that are heavily involved in carcinogenesis. Of note, 1131 radioactive decay takes place not only via Gamma decomposition but also via Beta. This further supports our finding that Yel compounds mitigate radiation-induced damage implicated in carcinogenesis from various quality of radiation.

Example 8

Reduction in the Frequency of Spontaneous Cancer

Certain predispositions, such as mutations in oncogenes and tumor suppressor genes (BRCA1/2, ATM, etc), abnormality in the DNA repair machineries, immune system deficiencies, infections with certain bacterial and viral pathogens, and hormonal imbalances increase the frequencies of spontaneous malignant neoplastic development. Despite of the different etiologies of the cancer formation all have one common denominator—genetic instability.

Yel001 and Yel002 have shown genetic stabilization properties—DEL frequency reduction, mitigation of radiation-induced leukemia, and absence of cancers in lethally irradiated mice—it is evident that these compounds also reduce the frequency of spontaneous cancers. FIG. 18 shows that both Yel001 and Yel002 are effective for reducing the frequency of spontaneous cancer.

Mitigation effects of Yel001 and Yel002 on radiation-induced cancer of the proliferating hematopoietic cells are translatable into other radiation (or UV)-induced cancer models of proliferating tissues such as skin and intestinal lining.

Beyond the mentioned public safety concerns are the clinical implications of radiation use. About half of all cancer patients receive some type of radiation therapy and many receive multiple forms of radiation when treated. According to the American Cancer Society, the number of cancer cases in 2009 within the United States alone is over 1,400,000 which would amount to more than 700,000 individuals exposed to therapeutic doses of radiation on an annual basis. The compounds disclosed herein protect normal tissues which may have a major clinical impact including but not limited to the following: increased capacity of a patients to receive radiation, IR (irradiation) treatment of normal tissues to ablate microscopic tumors, protecting patients from large amounts of IR exposure in a clinical setting, novel radiation treatment plans amongst other related uses.

Example 9

Combinatorial Treatment

The non-toxic nature of Yel001 and Yel002 make these two agents good combinatorial treatment options with other life-supporting therapies necessary post radiation exposures. Yel001 and Yel002 can supplement each other in the mitigation protocols presented above or in combinations with other agents such as Amifostine, free radical scavengers, growth factors, immune modulators, anti-apoptotic agents, or capture agents, et cetera.

Example 10

Modulation of Genetic Instabilities Associated with Aging

Genomic instability is one of the hallmarks of aging (senescence). Events such as genome rearrangement, deletion and point mutations, epigenetic modifications, erroneous DNA repairs, et cetera accumulate in the cells and eventually lead either to cell death, failure to replicate, or carcinogenesis. In numerous in vitro and in vivo models, including yeast (Saccharomyces cerevisiae), fruit fly (Drosophila melanogaster), and mouse (Mus musculus) it has been shown that maintaining genomic integrity leads to higher regenerative potential in cells and overall increases longevity.

While some underlying causes of genetic instability and consequently aging are intrinsic (hormonal imbalances), most of the causes are extrinsic/environmental (oxidative stress, exposure to tobacco smoke, diesel exhaust).

As identified with the yeast-based DEL assays, Yel001 and Yel002 compounds confer genetic stability even after such an extreme assault on the genome as ionizing radiation. Drawing the parallel between genetic instability associated with aging and genetic instability associated with radiation exposure it is logical that Yel001 and Yel002 small molecules modulate the aging process on the cellular level by promoting the integrity of the genome.

Example 11

Mitigation Effects of a Number of Yel001 and Yel002 Analogs

Figure 19A:
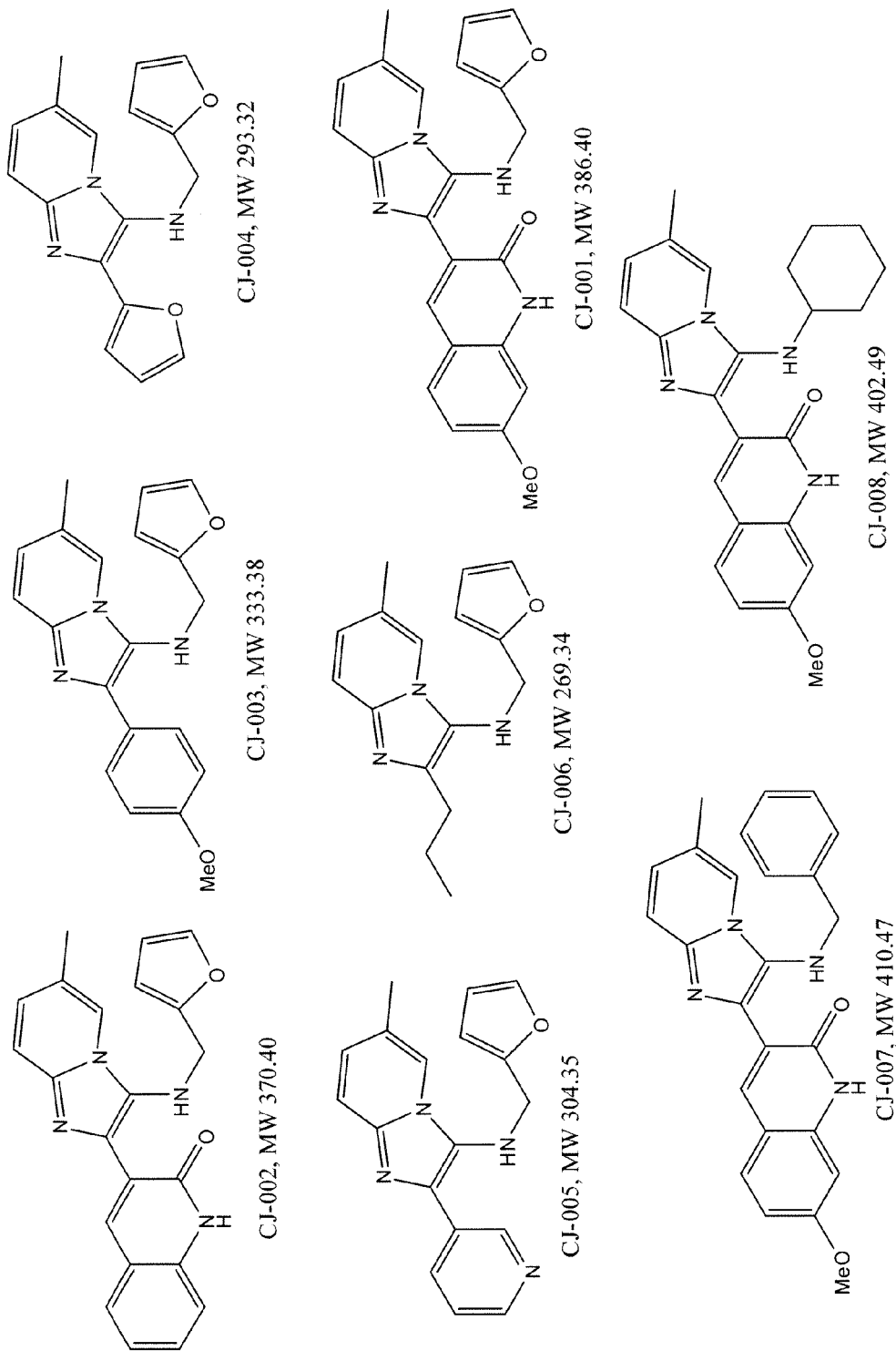
FIGS. 19A and 19B show structures of some compounds of Formula I or Formula II.
Figure 19B:
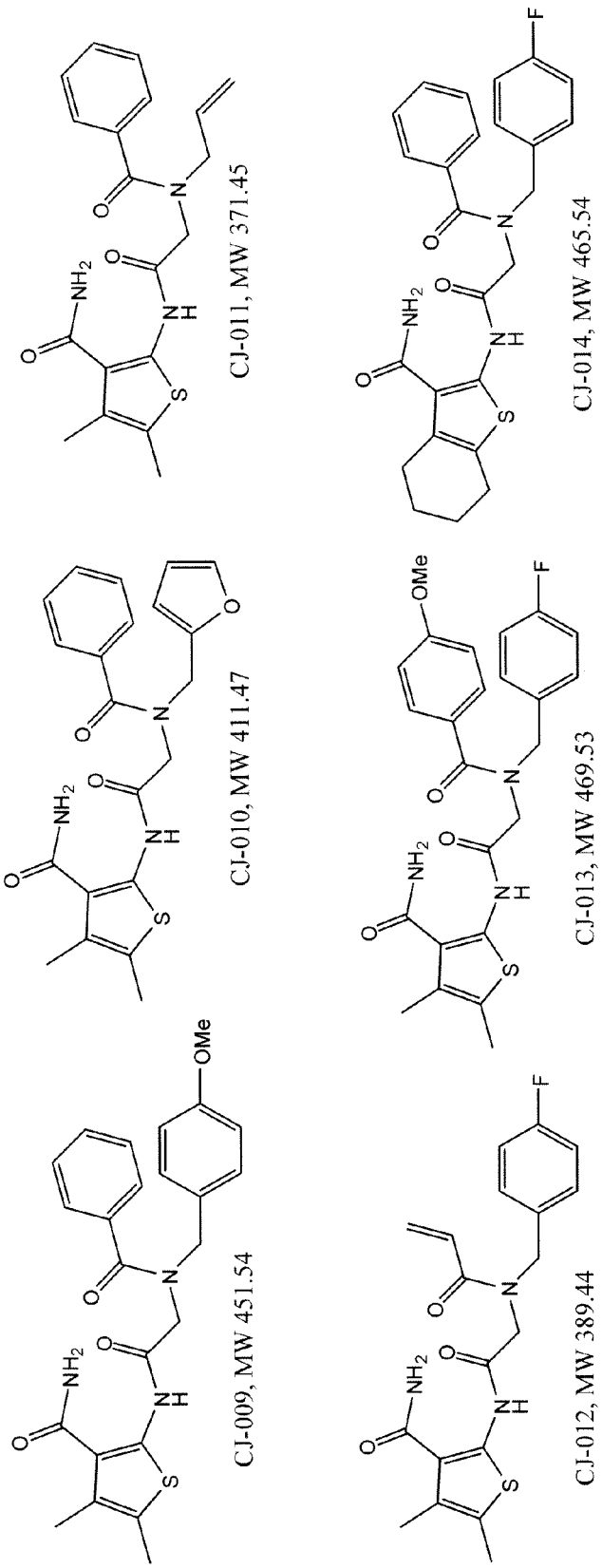

Fourteen analogs of Yel001 and Yel002, whose structures are shown in FIGS. 19A and 19B, are subject to tests in a mitigation assay at +30 min and +60 min after 8 Gy radiation (IR). The results are shown in FIG. 20.

Figure 20:
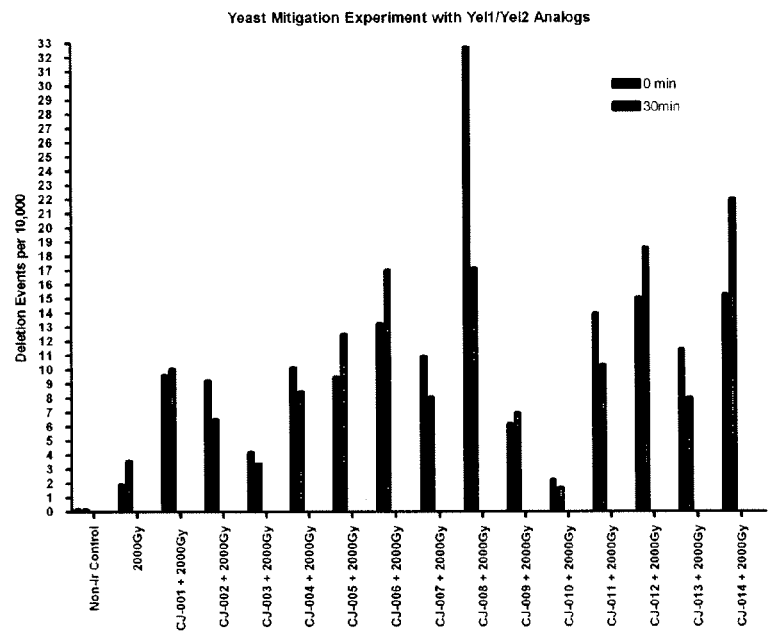
FIG. 20 shows that CJ010 consistently mitigates the IR damage.

FIG. 20 shows that CJ010 consistently mitigates the IR damage.

Figure 21:
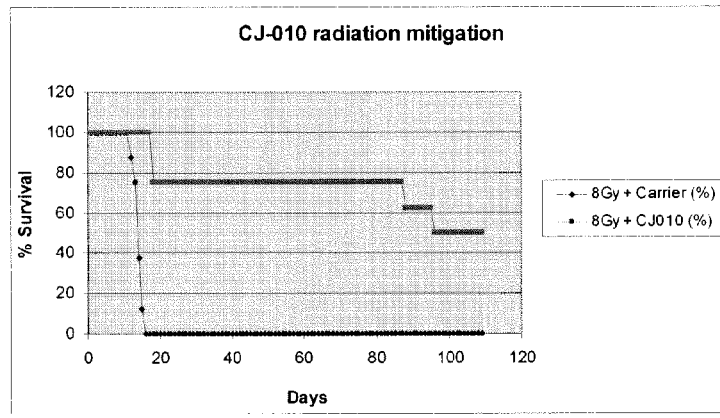
FIG. 21 shows the results of tests on radiation mitigation effect of CJ-010.

Additionally, CJ010 is subject to an in vivo assay under the same conditions as are the other compounds (5×24) 75 mg/kg s.c. (C3H mice). The results are shown in FIG. 21, which shows, at 30 days after IR (8 Gy) subjects receiving CJ010 have a 75% survival rate as compared with 0% survival rate for controls without CJ010.

Examples 12-13

Studies on Mitigation of Radiation Induced Lethality with Oral Administration of Yel002 In Vivo

Example 12

In addition to previously described subcutaneous (s.c.) administration of Yel002 following 8Gy (LD100/30) irradiation at 24, 48, 72, 96, and 120 hrs (5×24), Yel002 has also been administered orally (gavage) on the same administration schedule with a success rate of 33% versus 75% survival with s.c. administration.

Figure 23:
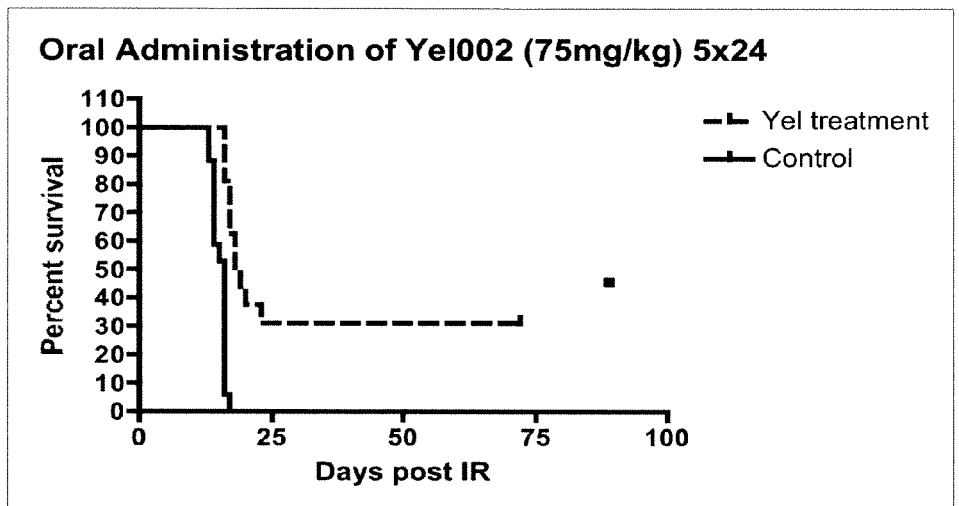
FIG. 23 shows survival of C3H mice (n=16) following 8 Gy irradiation and treatment with Yel002 (oral gavage in saline) at 24, 48, 72, 96, and 120 hrs.

FIG. 23 shows survival of C3H mice (n=16) following 8 Gy irradiation and treatment with Yel002 (oral gavage in saline) at 24, 48, 72, 96, and 120 hrs. Controls received saline carrier only. $P<0.001$. In FIG. 23, the dose modifying factor (DMF) for Yel002 following radiation exposure is 1.15 at LD50/30.

Figure 24:
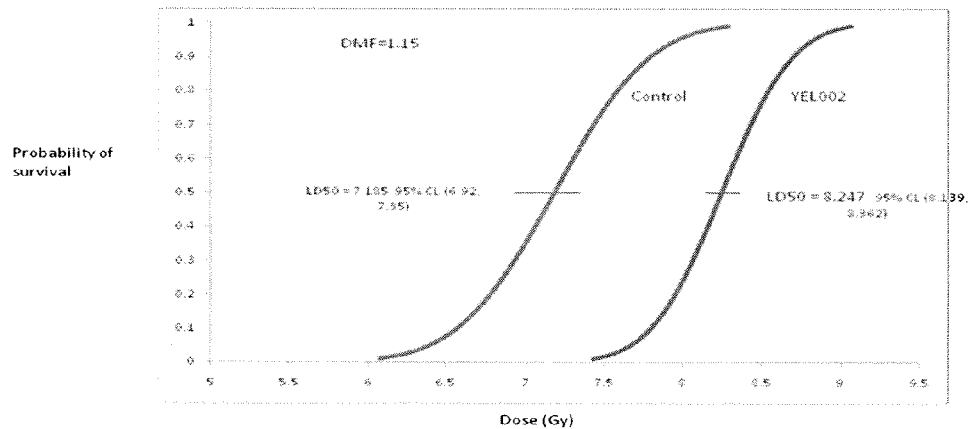
FIG. 24 shows male C3H mice (n=8, per irradiation group) were exposed to increasing doses of radiation (7Gy to 9.1 Gy, increments of 0.3Gy) and treated with Yel002 (75 mg/kg) at 5×24 s.c. administration.

FIG. 24 shows male C3H mice (n=8, per irradiation group) were exposed to increasing doses of radiation (7Gy to 9.1 Gy, increments of 0.3Gy) and treated with Yel002 (75 mg/kg) at 5×24 s.c. administration. Controls received saline carrier injections.

Example 13

Yel002 was found to promote the recovery of the hematopoietic system when administered after irradiation on the 5×24 hr schedule at 75 mg/kg. Treatment with Yel002 increases the recovery of total white blood cells, red blood cells, and platelets.

Figure 25:
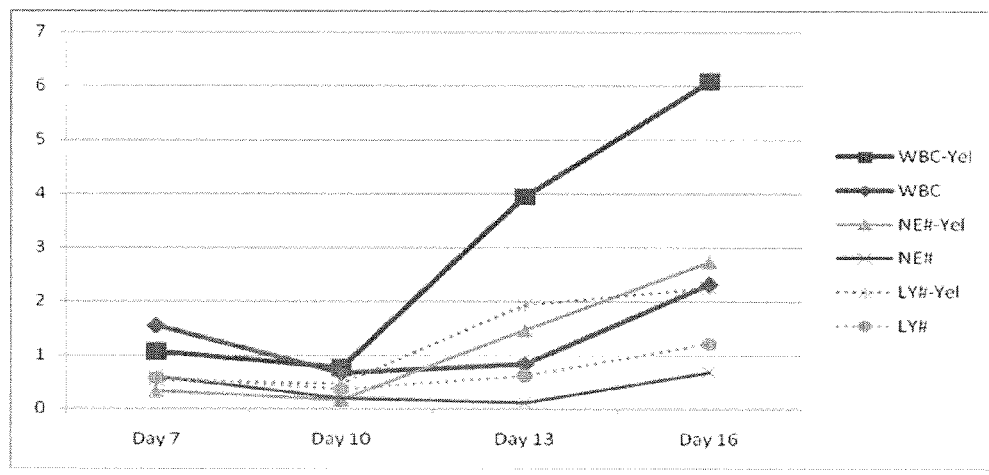
FIG. 25 shows recovery of the hematopoietic system following 6 Gy irradiation of C3H mice (n=4) with Yel002 treatment (s.c.) at 24, 48, 72, 96, and 120 hrs.

FIG. 25 shows recovery of the hematopoietic system following 6 Gy irradiation of C3H mice (n=4) with Yel002 treatment (s.c.) at 24, 48, 72, 96, and 120 hrs. WBC-total white blood cells (K/uL), NE—neutrophils (K/uL), and LY—lymphocytes (K/uL). With 1—tail, Student's t-Student's t-test, WBC and NE, along with monocytes, eosinophils, and basophils (data not shown) are p<0.05.

Figure 26:
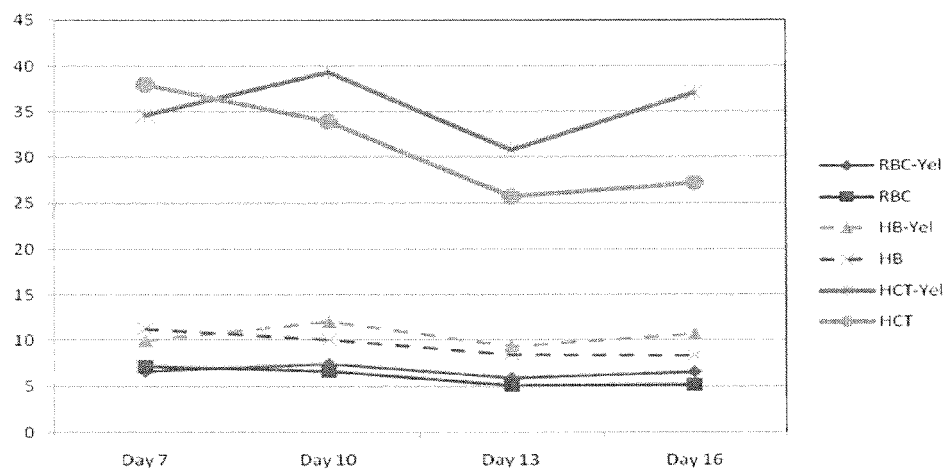
FIG. 26 shows recovery of the hematopoietic system following 6 Gy irradiation of C3H mice (n=4) with Yel002 treatment (s.c.) at 24, 48, 72, 96, and 120 hrs. RBC— red blood cells (M/μL), HB-hemoglobin (g/dL), and HCT-hematocrit (%).

FIG. 26 shows recovery of the hematopoietic system following 6 Gy irradiation of C3H mice (n=4) with Yel002 treatment (s.c.) at 24, 48, 72, 96, and 120 hrs. RBC— red blood cells (M/uL), HB-hemoglobin (g/dL), and HCT-hematocrit (%).

Figure 27:
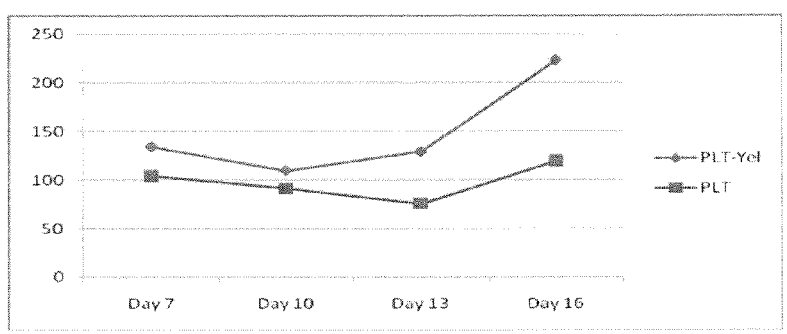
FIG. 27 shows platelet recovery following 6 Gy irradiation of C3H mice (n=4) with Yel002 treatment (s.c.) at 24, 48, 72, 96, and 120 hrs; p<0.05 with a 1-tail, Student t-test.

FIG. 27 shows platelet recovery following 6 Gy irradiation of C3H mice (n=4) with Yel002 treatment (s.c.) at 24, 48, 72, 96, and 120 hrs; p<0.05 with a 1-tail, Student t-test.

Example 14

Mitigation of Ultraviolet (UV) Radiation-Induced Damage

UV radiation is recognized as the main etiological agent responsible for carcinogenesis (being a tumor initiator and promoter) and aging in the skin. UV radiation results in generating essentially the same genotoxic, prolonged genetic instability, and cytotoxicity profile as that of ionizing radiation: DNA single strand breaks, DNA cross-linking, nucleotide base modification, cell cycle checkpoint bypass, apoptosis initiation, etc. Additionally, molecular pathways activated by UV exposures are very similar to those induced by ionizing radiation assault.

In vitro and in vivo experiments with Yel001 and Yel002 have demonstrated mitigation and protection against the damages induced by ionizing radiation. Based on these studies and the similarity between the radiation profiles it is evident that Yel001 and Yel002 can protect, mitigate, and ameliorate UV-associated injuries.

Figure 28:
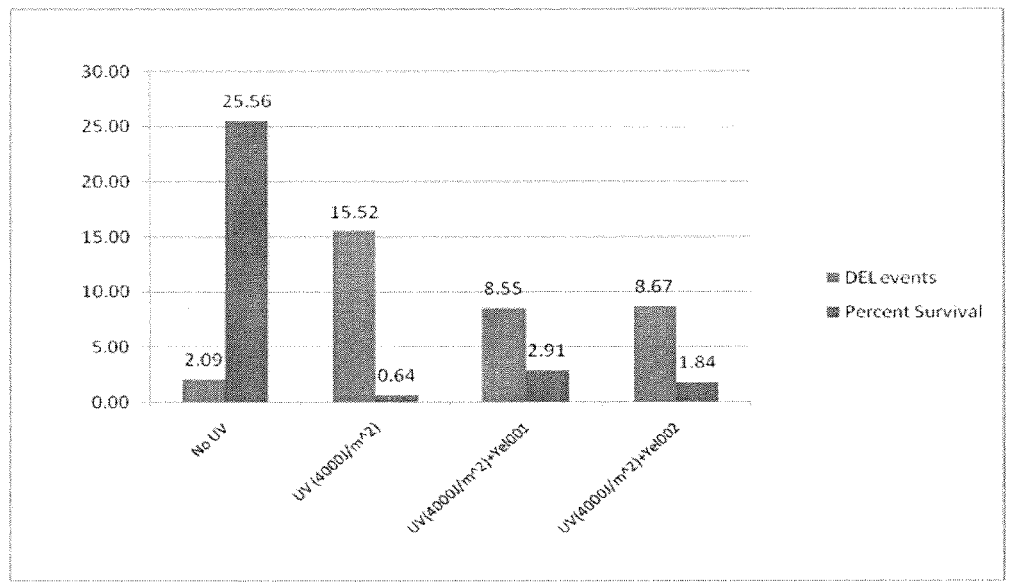
FIG. 28 shows addition of Yel002 and Yel001 (15 uM) to UV-irradiated yeast DEL tester strain RS112 significantly reduces genotoxicity and cytotoxicity; P<0.05.

Tests in this example show administration of Yel001 and Yel002 reduces cell death and genotoxicity associated with exposure to Ultraviolet (UV) radiation in vitro (FIG. 28).

DEL tester strain was irradiated with 4000 J/m$^2$ in the ultraviolet range and treated with Yel001 or Yel002 at 60 minutes at the concentration of 15 uM. Treatment with the Yel compounds reduces the extent of genotoxicity by a factor of 1.8 and increases survival from 0.64% to 2.91% and 1.84 with Yel001 and Yel002 respectively.

FIG. 28 shows addition of Yel002 and Yel001 (15 uM) to UV-irradiated yeast DEL tester strain RS112 significantly reduces genotoxicity and cytotoxicity; P<0.05.

Example 15

Mitigation of DNA Damages by Smoking

Tests in this example show YEL 002 significantly reduces cigarette smoke induced double strand breaks at 6 and 24 hrs in Ogg−/− Myh−/− double knockout mice (FIGS. 29a and 29b).

Whole peripheral blood lymphocytes were taken from WT, and OMM double knockout mice (mice deficient in DNA repair pathways observed in smoking-induced lung cancer) and were administered 3 puff/mL of Cigarette smoke extract (CSE) alone or co-incubation of 3 puff/mL Cigarette smoke extract and 10 uM Yel 002 for 3, 6, and 24 hrs and the amount of double stranded breaks were assessed via γH2AX assay. Addition of Yel002 at 15 uM reduces the number of DNA double strand breaks (DSB).

FIG. 29a (left) shows a significant decrease in the amount of average γH2AX per cell in OMM lymphocytes at p<0.05. Statistical significance was assessed via a 1 way ANOVA test with Tukey's post-hoc analysis. FIG. 29b (right) shows that YEL 002 incubation significantly decreases the amount of average γH2AX per cell in OMM lymphocytes p<0.01. Statistical significance was assessed via a 1 way ANOVA test with Tukey's post-hoc analysis. N=3 in each group.

Example 16

Mitigation of Radiation Induced Lethality with CJ010 In Vivo

Tests in this example show that structural analog of Yel001, CJ010, on the same subcutaneous administration (75 mg/kg) at 5×24 administration schedule confers 75% survival (FIG. 30). FIG. 30 shows the results of tests where C3H (n=8 in each group) were irradiated and treated at the 5×24 treatment protocol with Yel001 and CJ-10 s.c. Controls received 1N saline carrier injections. At 30 days post IR, CJ-10 has significantly mitigated IR-induced damages and death. (p<0.05).

Example 17

Mitigation of Damage Induced by Chemical Carcinogens

A DEL assay, described above, is used for assessing mitigation of damage induced by chemical carcinogens by compounds of invention.

The classical DEL assay and a DEL assay adapted for high throughput screening have been used to identify Yel001 and Yel002 from a pool of small biologically active molecules for their ability to mitigate radiation-induced genotoxicity and cytotoxicity. Due to the DEL assay's ability to detect a variety of carcinogenic mechanisms and the Yel001's and Yel002's ability to ameliorate carcinogenic activity, Yel001 and Yel002 also protect against chemically-induced carcinogenesis. In the past the carcinogenicity of the agent was assessed by looking at the DEL frequency increase following the exposure to the compound of interest. Thus, reduction of chemically-induced DEL frequency increase in the presence of Yel001 or Yel002 compounds would indicate mitigation.

Tests in this example show administration of Yel001 and Yel002 confers reduction against chemical carcinogen Methyl methanesulfonate (MMS) in vitro. Addition of Yel001 and Yel002 (15 uM) to RS112, DEL tester strain shows reduction in genotoxicity and cytotoxicity associated with treatment with chemical mutagen EMS and carcinogen MMS.

FIG. 31 shows addition of MMS to DEL RS112 tester strain induces cell death and genotoxicity that can be mitigated with Yel001 and Yel002 administration 1 hrs after exposure to MMS. Reduction of cytotoxicity and genotoxicity with Yel002 is p<0.007 and p<0.04 restively; p-values for Yel001 are 0.0007 (genotoxicity) and 0.1 for cytotoxicity.

Example 18

Treatment with Yel002 Reduces Senescence Associated with Aging in vitro

Figure 32:
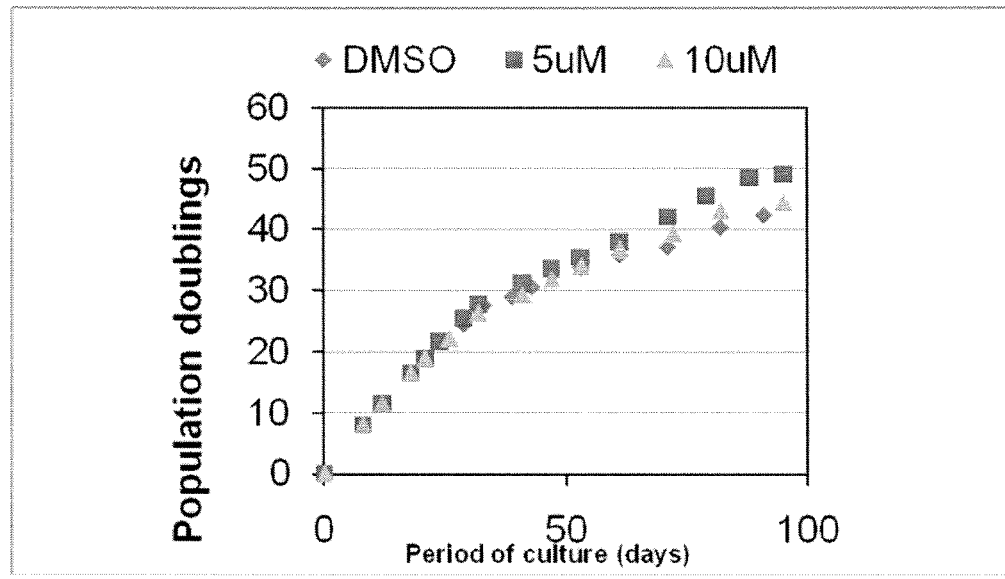
FIG. 32 shows co-culturing with Yel002 decreases the progression into senescence of primary human keratinocytes at 5 uM concentration of the drug.
Figure 33:
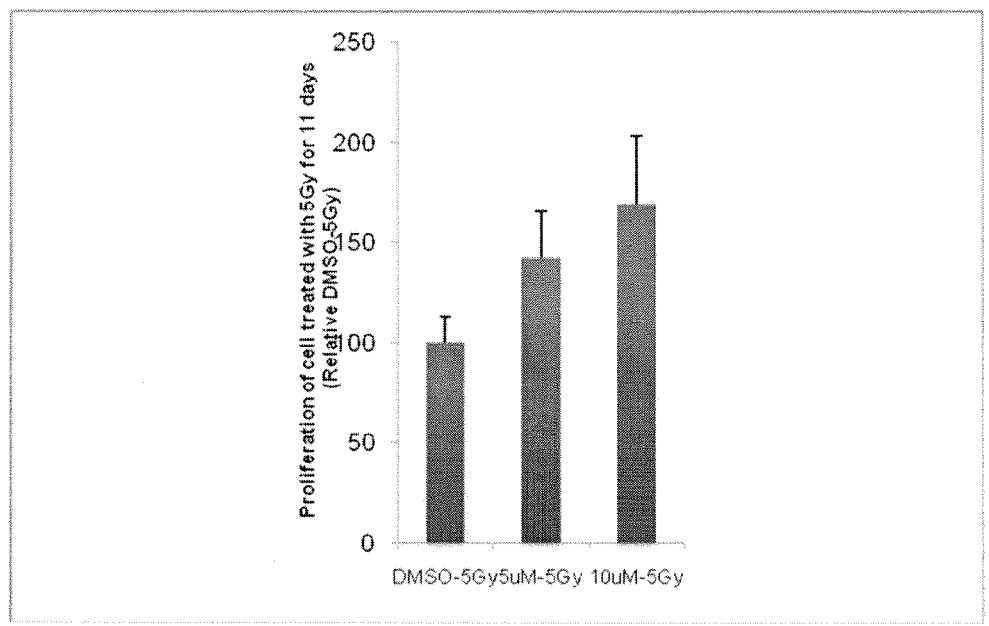
FIG. 33 shows primary keratinocytes harvested from a patient were isolated and propagated in culture until 5Gy irradiation.

Skin aging has been linked to senescence on the level of primary skin cells (Campisi, J., J Investig Dermatol Symp Proc, 1998. 3(1): p. 1-5) (FIGS. 32-33).

Addition of Yel002 to a culture of primary keratinocytes harvested from a patient extended the doubling time of the cells and decreased progression of cells into senescence.

FIG. 32 shows co-culturing with Yel002 decreases the progression into senescence of primary human keratinocytes at 5 uM concentration of the drug.

Additionally, co-culture of primary keratinocytes exposed to 5Gy of radiation, an event that induces senescence, with Yel002 at the concentration of 5 uM increased proliferation as compared to controls.

FIG. 33 shows primary keratinocytes harvested from a patient were isolated and propagated in culture until 5Gy irradiation. After the IR the cells were treated with Yel002 and cultured for 11 days.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

We claim:

1. A method of mitigating tissue damage, genetic instability, or lethality induced by radiation or a chemical carcinogen in a cell, the method comprising contacting the cell with a compound having a structure of Formula IA

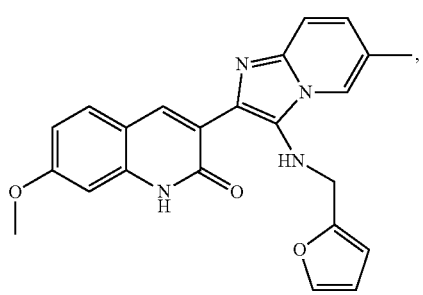

Formula IA or a pharmaceutically acceptable salt thereof.

2. The method according to claim 1, wherein the compound is administered in a pharmaceutical composition that further comprises a pharmaceutically acceptable excipient.

3. The method of claim 1, wherein said tissue damage, genetic instability, or lethality is induced by radiation and the radiation is selected from radiation emitted by a radioactive element, alpha radiation, beta radiation, gamma radiation, neutron radiation, x radiation, and ultraviolet radiation.

4. The method according to claim 1, wherein the tissue damage, genetic instability, or lethality is induced by exposure to radiation from a nuclear reactor.

5. The method according to claim 2, wherein the composition further comprises a second agent.

6. The method according to claim 5, wherein the second agent is a therapeutic agent.

7. The method according to claim 6, wherein the second agent is selected from amifostine, free radical scavengers, growth factors, immune modulators, anti-apoptotic agents and/or capture agents.

8. The method according to claim 2, wherein 0.05% to 10 wt % of the composition is an active ingredient.

9. The method according to claim 1, wherein the method reduces cell death or genetic instability by a percentage of 5% or higher.

10. The method according to claim 1, wherein the method reduces cell death or genetic instability by a percentage of 10% or higher.

11. The method according to claim 1, wherein the method reduces cell death or genetic instability by a percentage of 25% or higher.

12. The method according to claim 1, wherein the method reduces cell death or genetic instability by a percentage of 50% or higher.

* * * * *